(12) United States Patent
Fisher et al.

(10) Patent No.: US 8,672,943 B2
(45) Date of Patent: Mar. 18, 2014

(54) SURGICAL SAW BLADE DEVICE AND SYSTEM

(75) Inventors: Michael Fisher, Folsom, CA (US); Barjinder Chana, Rancho Cordova, CA (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 404 days.

(21) Appl. No.: 12/464,825

(22) Filed: May 12, 2009

(65) Prior Publication Data

US 2010/0292701 A1    Nov. 18, 2010

(51) Int. Cl.
*A61B 17/00* (2006.01)

(52) U.S. Cl.
USPC .......................................................... 606/82

(58) Field of Classification Search
USPC .......... 606/79, 82–85, 167–186; 30/143, 151, 30/155
See application file for complete search history.

(56) References Cited

U.S. PATENT DOCUMENTS

| | | | |
|---|---|---|---|
| 1,179,910 A | 4/1916 | Greenfield | |
| 1,201,467 A | 10/1916 | Hoglund | |
| 1,726,241 A | 8/1929 | Schubert | |
| 2,702,550 A | 2/1955 | Rowe | |
| 2,854,981 A | 10/1958 | Morrison | |
| 3,554,197 A | 1/1971 | Dobbie | |
| 3,678,934 A | 7/1972 | Warfield et al. | |
| 3,978,862 A | 9/1976 | Morrison | |
| 4,513,742 A | 4/1985 | Arnegger | |
| 4,567,798 A | 2/1986 | Brdicko | |
| 4,584,999 A | 4/1986 | Arnegger | |
| 4,617,930 A | 10/1986 | Saunders | |
| 4,768,504 A | 9/1988 | Ender | |
| 5,087,261 A | 2/1992 | Ryd et al. | |
| 5,092,869 A | 3/1992 | Waldron | |

(Continued)

FOREIGN PATENT DOCUMENTS

| | | |
|---|---|---|
| DE | 202006009423 U1 | 9/2006 |
| DE | 202008017023 U1 | 4/2009 |
| DE | 202008017026 U1 | 4/2009 |
| WO | WO 2007/030793 A2 | 3/2007 |

OTHER PUBLICATIONS

Stryker® Precision Oscillating Tip Saw—Ref 6209, Instruction for Use, Sep. 2006, 21 pages total.

(Continued)

*Primary Examiner* — Nicholas Woodall
(74) *Attorney, Agent, or Firm* — Seager, Tufte & Wickhem, LLC

(57) ABSTRACT

A saw blade assembly for use with a driver having an oscillatory drive member comprises an elongate sheath and an elongate monolithic blade. The sheath's proximal end is removably mountable on the driver. The sheath has an open interior which receives the blade. The blade's proximal end is pivotably mounted to the sheath's proximal end. The blade's distal cutting end extends out of the sheath's distal end and is transverse to the blade's central longitudinal axis. When cutting bone, the drive member pivots the blade's cutting end back and forth in an arc about a pivot point at the blade's proximal end while the driver holds the sheath stationary to protect surrounding tissues from the motions of the remainder of the blade. The long pivot radius between the proximal pivot point and the distal cutting end contributes to minimizing the angle of engagement of the cutting end to the bone.

37 Claims, 23 Drawing Sheets

(56) References Cited

U.S. PATENT DOCUMENTS

| | | | |
|---|---|---|---|
| 5,122,142 A | 6/1992 | Pascaloff | |
| 5,178,626 A | 1/1993 | Pappas | |
| 5,201,749 A | 4/1993 | Sachse et al. | |
| 5,263,972 A | 11/1993 | Evans et al. | |
| 5,306,285 A | 4/1994 | Miller et al. | |
| 5,382,249 A | 1/1995 | Fletcher | |
| 5,403,318 A | 4/1995 | Boehringer et al. | |
| 5,409,491 A | 4/1995 | Boehringer et al. | |
| 5,439,472 A | 8/1995 | Evans et al. | |
| 5,496,325 A | 3/1996 | McLees | |
| 5,507,763 A | 4/1996 | Petersen et al. | |
| 5,554,165 A | 9/1996 | Rait et al. | |
| 5,569,257 A | 10/1996 | Arnegger | |
| 5,735,866 A | 4/1998 | Adams et al. | |
| 5,839,196 A | 11/1998 | Trott | |
| 5,846,244 A | 12/1998 | Cripe | |
| 6,022,353 A | 2/2000 | Fletcher et al. | |
| 6,503,253 B1 | 1/2003 | Fletcher et al. | |
| 6,514,259 B2 | 2/2003 | Picard et al. | |
| 6,656,186 B2 | 12/2003 | Meckel | |
| 6,723,101 B2 | 4/2004 | Fletcher et al. | |
| 6,846,230 B2 | 1/2005 | Jonas | |
| 6,875,222 B2 | 4/2005 | Long et al. | |
| 6,896,679 B2 | 5/2005 | Danger et al. | |
| 7,497,860 B2 | 3/2009 | Carusillo et al. | |
| 7,527,628 B2 | 5/2009 | Fletcher et al. | |
| 7,704,254 B2 | 4/2010 | Walen | |
| 2002/0116022 A1 | 8/2002 | Lebouitz et al. | |
| 2002/0198556 A1* | 12/2002 | Ark et al. | 606/178 |
| 2003/0014067 A1 | 1/2003 | Kullmer et al. | |
| 2003/0075162 A1 | 4/2003 | Hamilton | |
| 2004/0199167 A1* | 10/2004 | Fletcher et al. | 606/79 |
| 2004/0243136 A1 | 12/2004 | Gupta et al. | |
| 2005/0065530 A1 | 3/2005 | Stauch et al. | |
| 2006/0009796 A1* | 1/2006 | Carusillo et al. | 606/178 |
| 2007/0083209 A1* | 4/2007 | Schenberger et al. | 606/82 |
| 2007/0119055 A1* | 5/2007 | Walen et al. | 30/144 |
| 2007/0123893 A1* | 5/2007 | O'Donoghue | 606/82 |
| 2008/0027449 A1* | 1/2008 | Gundlapalli et al. | 606/82 |
| 2008/0119860 A1 | 5/2008 | McCarthy | |
| 2008/0243125 A1 | 10/2008 | Guzman et al. | |
| 2009/0093814 A1 | 4/2009 | Fletcher et al. | |
| 2009/0093815 A1 | 4/2009 | Fletcher et al. | |

OTHER PUBLICATIONS

Stryker Precision™ Oscillating Tip Saw [pamphlet], 2006, 2 pages total.

U.S. Appl. No. 29/335,690, filed Apr. 20, 2009; First Named Inventor: Michael Fisher.

International Search Report and Written Opinion of PCT Application No. PCT/US2010/033143, mailed Jul. 2, 2010, 10 pages total.

* cited by examiner

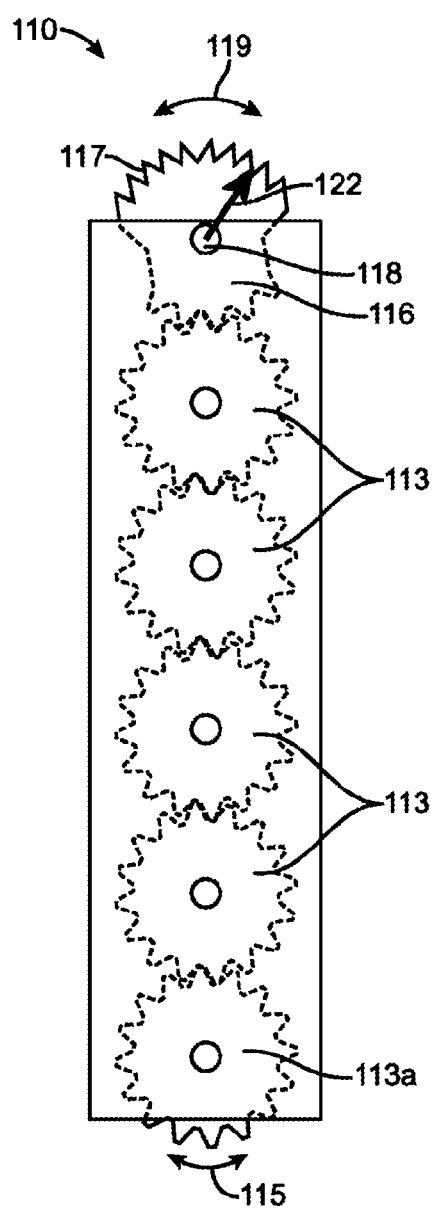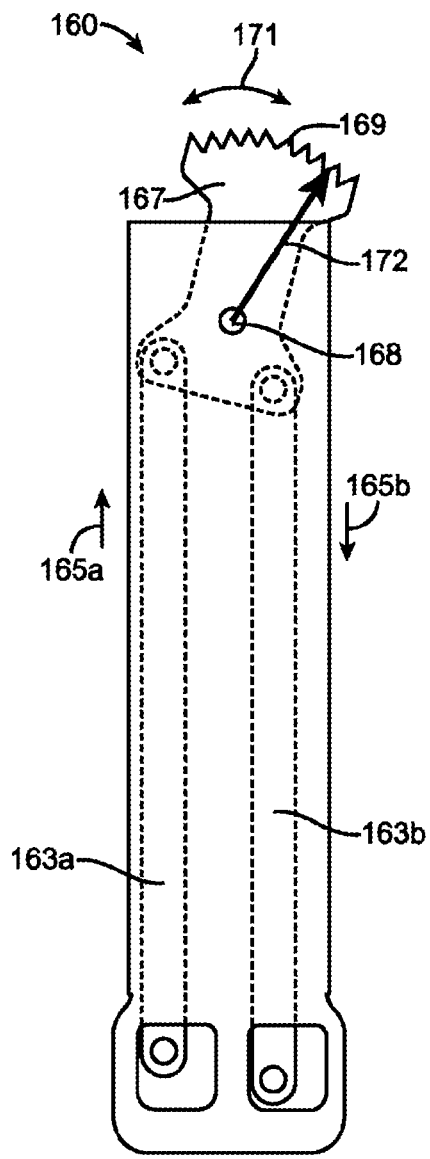
FIG. 1A
(PRIOR ART)
FIG. 1B
(PRIOR ART)

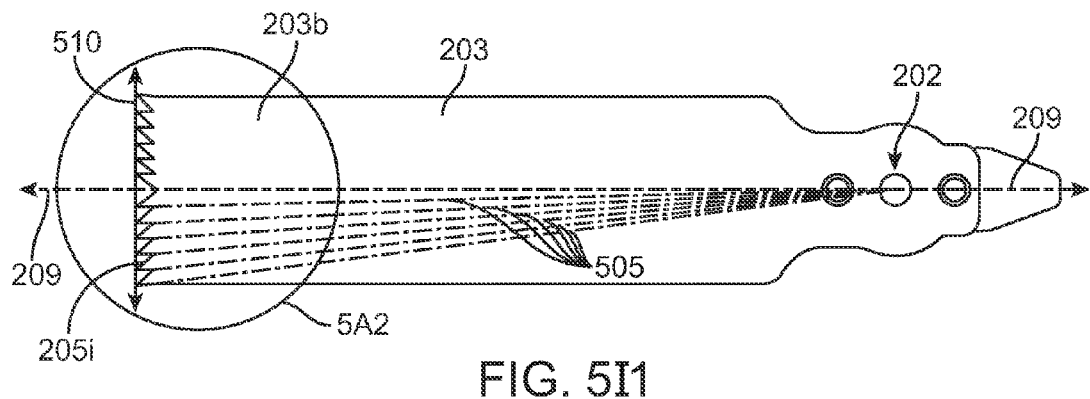
FIG. 5I1
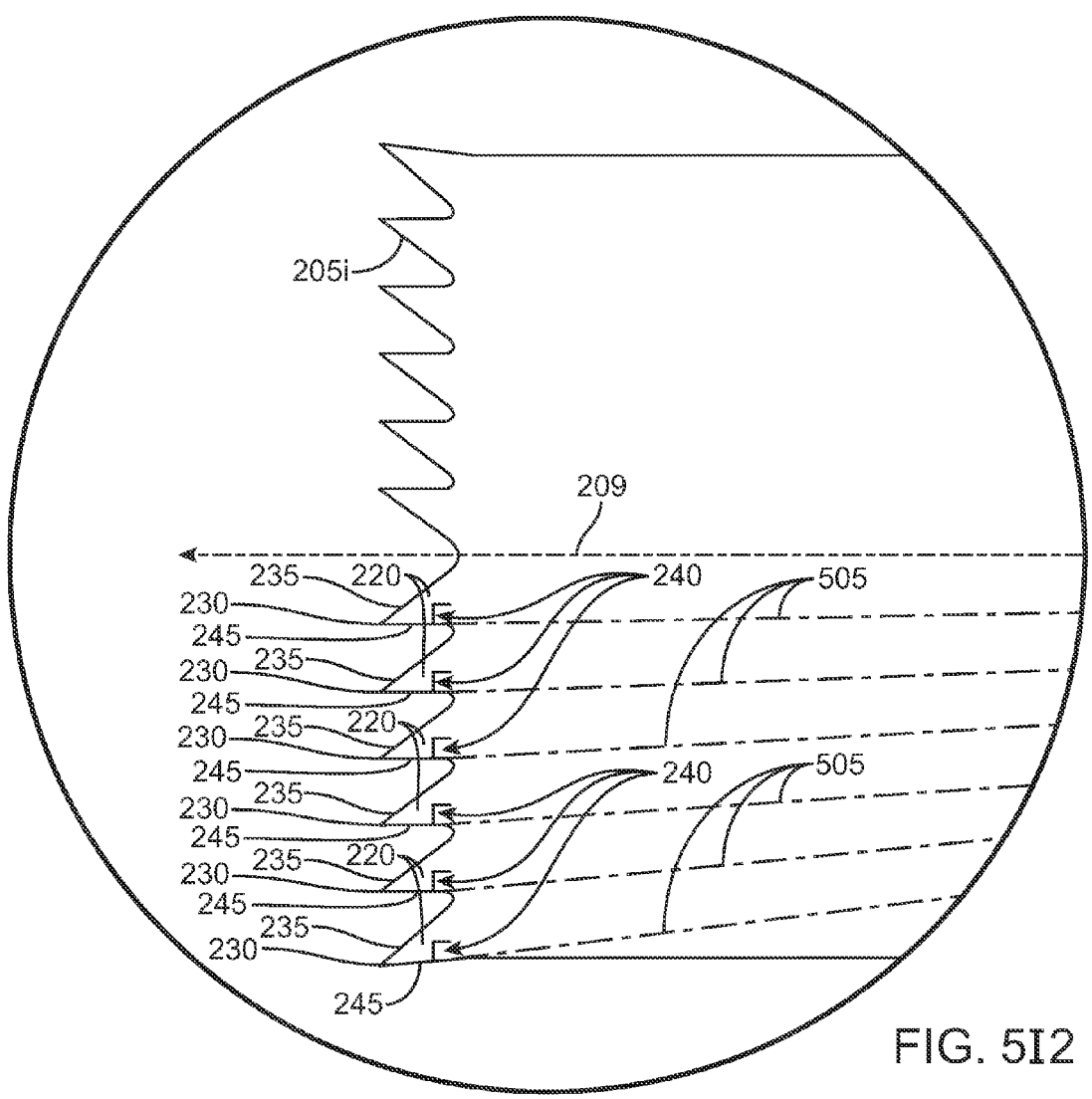
FIG. 5I2

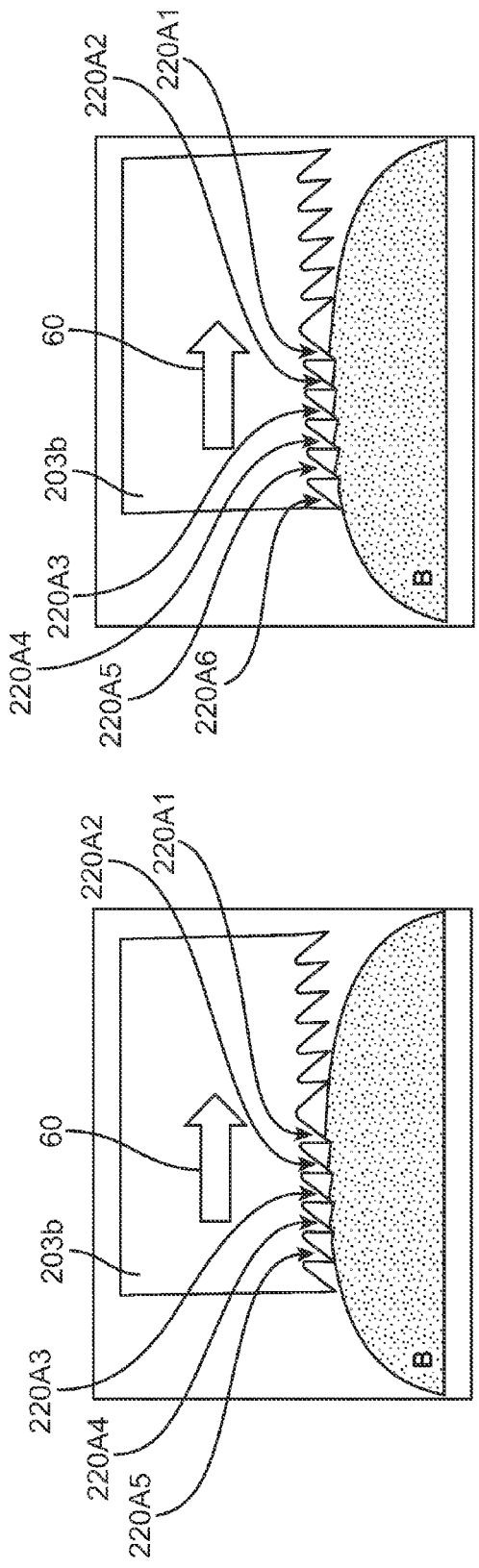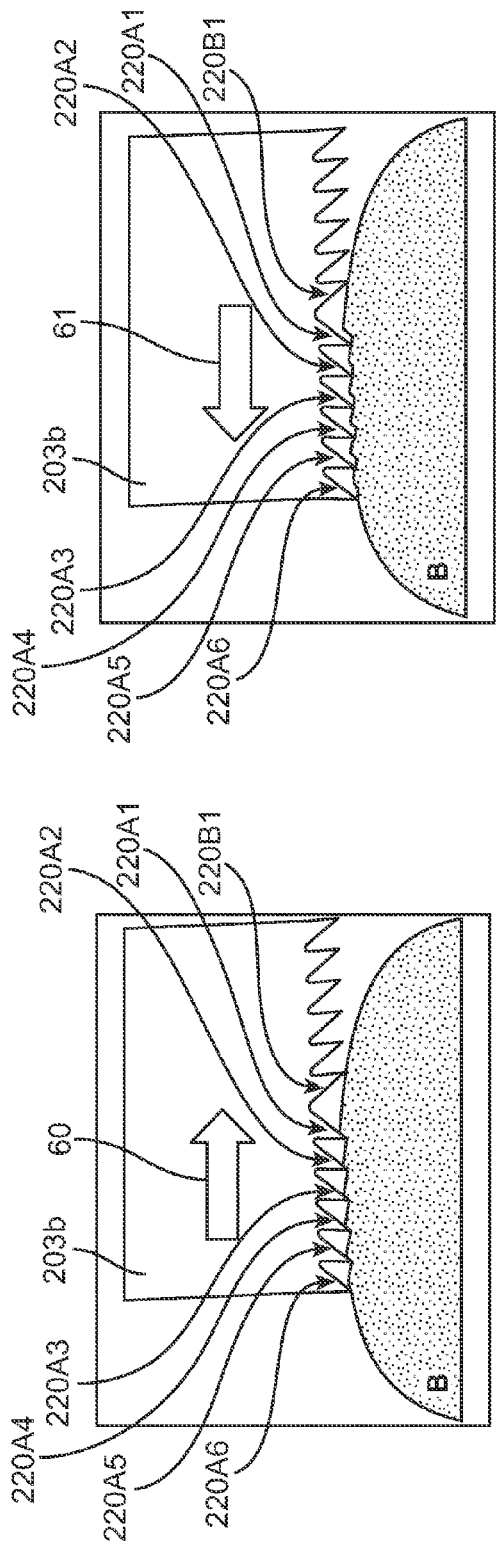

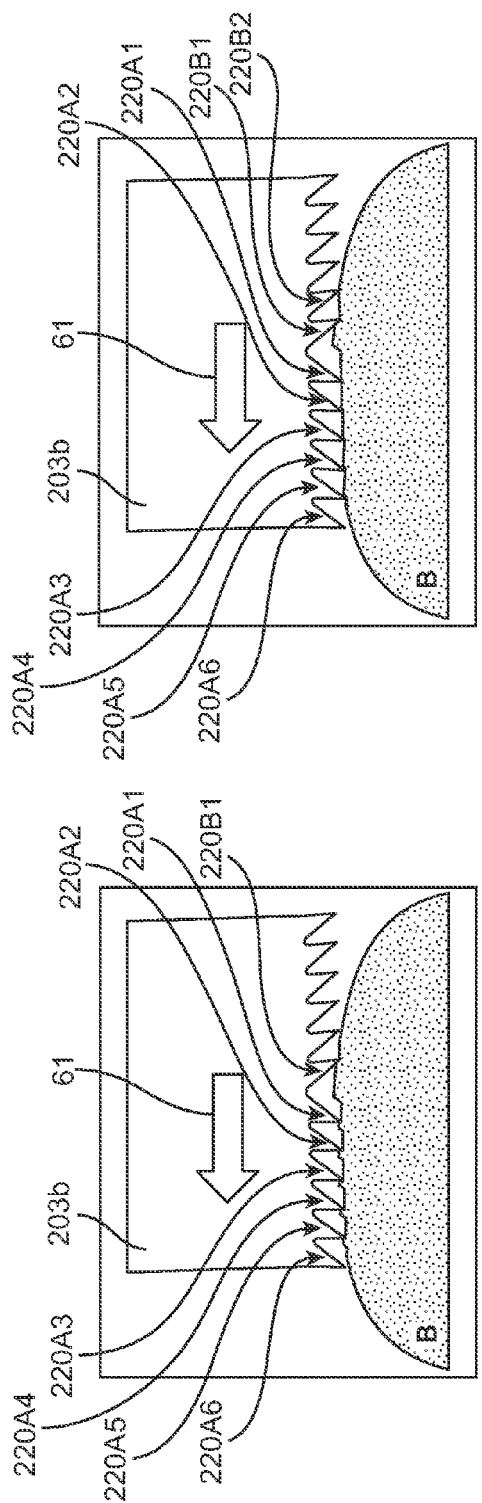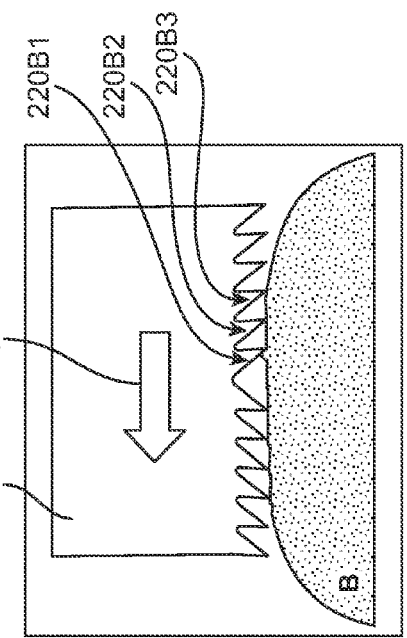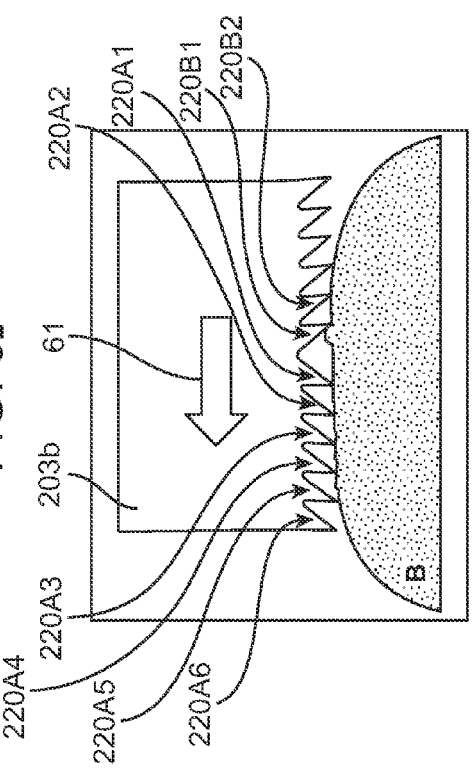

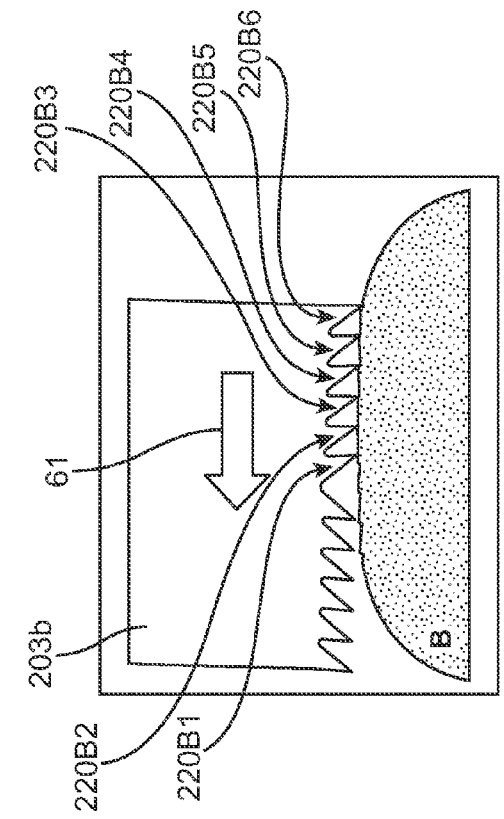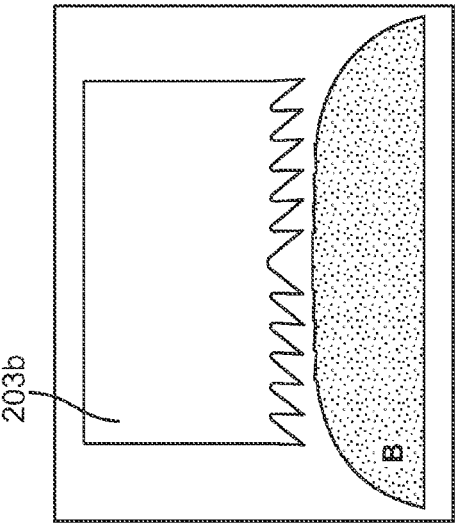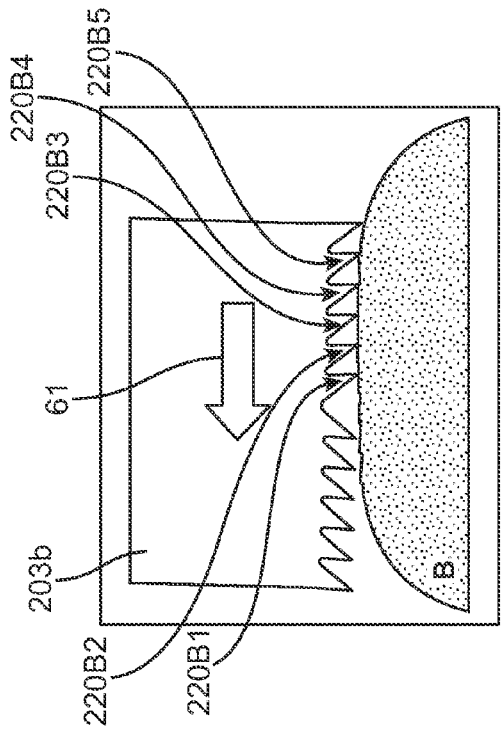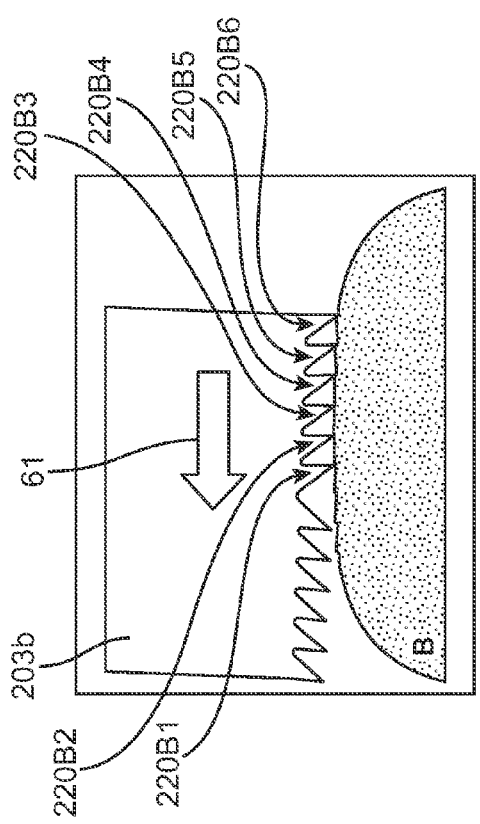

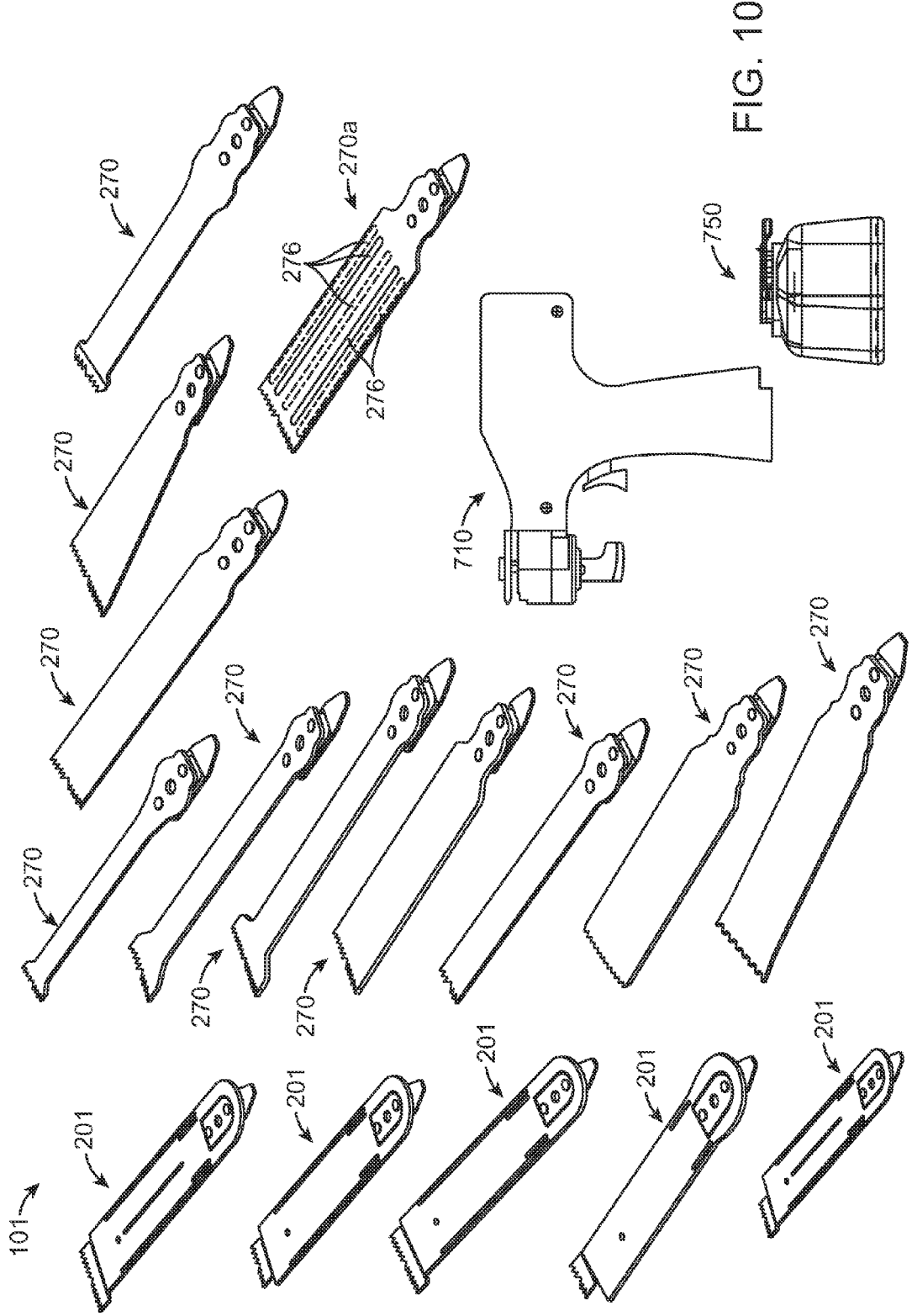

SURGICAL SAW BLADE DEVICE AND SYSTEM

BACKGROUND OF THE INVENTION

1. Field of the Invention

The following invention relates generally to instruments for cutting bone during surgery. More particularly, the instant invention is directed toward surgical saw blades adapted to be operatively coupled to powered surgical instruments.

2. Description of the Prior Art

Powered oscillating surgical saws with coupled bone cutting surgical saw blades are widely used in orthopedic surgery. Surgeons have long faced the problem of reaching narrow and deep recesses with power-driven surgical saw blades. During surgery, the protection of soft tissue such as tendons, ligaments, muscles, vascular and neurological structures is crucial. As such, various power transmission mechanisms, which transmit power from the proximally (near the surgeon or user) disposed powered oscillating surgical saw to the distal (far end) cutting edge of the surgical saw blade, have been designed to limit the midline oscillatory excursion of the distal cutting edge, i.e., limit the cutting action of the distal cutting edge, thereby reducing the exposure of adjacent soft tissue structures to the high-speed oscillatory excursion of the surgical saw blade.

Such known power transmission mechanisms can include translation mechanisms, for example, the translation mechanisms described in U.S. Pat. Nos. 1,179,910, 2,854,981 and 7,497,860. Translation mechanisms typically include moving internal parts which transmit motion from an attached powered oscillating surgical saw to a distal pivoting cutting edge. For example, as shown in FIG. 1A, a known surgical saw blade assembly 110 may include a plurality of linked gears 113. A connected powered oscillating surgical saw can rotate the proximal most gear 113a in a small arc 115. The resulting motion is transmitted through the plurality of linked gears 113, causing distal cutting member 116 to oscillate about a distally disposed center of oscillation or pivot point 118 and moving the distal toothed cutting edge 117 in a small arc 119. The pivot radius 122 of the distal cutting member 116 extends from the distally disposed center of oscillation 118 to the distal tips of the teeth of distal toothed cutting edge 117. Another example is shown in FIG. 1B, which shows a known surgical saw blade assembly 160 which comprises a pair of push rods 163a and 163b. To move the distal cutting edge 169 in a small arc 171, the first push rod 163a is driven in one direction, for example, as indicated by arrow 165a, while the second push rod 163b is driven in the opposite direction, for example, as indicated by arrow 165b. This reciprocating action of the push rods 163a, 163b causes the distal toothed cutting member 167 to oscillate about a distally disposed center of oscillation or pivot point 168. The pivot radius 172 of the distal toothed cutting member extends from the distally disposed center of oscillation 168 to the distal tips of the cutting edge 169.

These translation mechanisms are not without their disadvantages. With every additional moving component within a translation mechanism, there typically needs to be adequate dimensional clearance provided between the moving internal parts to allow them to move. By providing for such required freedom of motion, efficiency can be lost in such translation mechanisms. Furthermore, surgical saw blades typically operate at about 10,000 cycles per minute. Thus, much friction between the moving internal parts can be created when the surgical saw blade is in use. As such, efficiency can further be lost between the power source and the cutting edge of the surgical saw blade with a translation mechanism.

Additionally, these translation mechanisms often require their cutting edges to pivot from a distally disposed pivot point, for example pivot points 118 and 168 as shown in FIGS. 1A and 1B, respectively. As a result, the teeth of the cutting edges engage bone at a very sharp and unstable angle. This sharp, unstable engagement angle can cause the surgical saw blade to buck and "kick", i.e., become caught upon the bone being cut by the point of a tooth. This tendency of the surgical saw blade to buck and "kick" will typically reduce the overall cutting efficiency and accuracy of the saw blade assembly. The instability of the surgical saw blade can also translate back to the surgeon's hand, increasing the risk of an inaccurate bone cut. In at least some cases, the surgeon may be able to rein in the instability by maintaining a tighter grip on the proximally disposed powered oscillating surgical saw. However, maintaining a tighter grip increases the fatigue of the surgeon and the instability can manifest itself as torsional stresses placed upon the moving parts of the saw blade assembly.

In the specific cases of translation mechanisms incorporating reciprocating push rods, for example, the translation mechanisms shown in FIG. 1B and those described in U.S. Pat. Nos. 2,854,981 and 7,497,860, such torsional stresses may cause binding of the long push rods against the stationary components of the saw blade assembly. With the saw blade assembly operating at high speeds, for example, approximately 10,000 to 14,000 cycles per minute, such binding can cause additional friction between the push rods and the stationary elements of the saw blade assembly. This additional friction creates heat and can cause the moving portions of the saw blade assembly to slow down, further reducing the cutting efficiency of the cutting edge. If such binding starts to occur, a surgeon may mistake the resulting increased resistance as cutting resistance from the bone and push harder on the saw blade. Pushing harder on the saw blade assembly increases the very undesirable possibility of the saw blade skiving upwardly, which causes an inaccurate bone cut. Worse yet, the saw blade may dive deeper into the bone, well beyond the intended bone resection level.

Thus, known bone cutting surgical saw blades incorporating such translation mechanisms may not be ideal for efficiently and stably engaging and cutting bone at high speeds. Due to their multitude of moving internal parts, they can be mechanically inefficient. These known surgical saw blades can further be hampered by increased frictional forces caused by torsional stresses placed upon the saw blade assembly.

Other surgical saw blades without complicated translation mechanisms are also well known. These saw blades are described, for example, in co-assigned U.S. Pat. Nos. 6,022,353, 6,503,253, 6,723,101, and 7,527,628, the entire contents of which are incorporated by reference herein. Such saw blades are well-accepted in the orthopedic industry as having optimal bone cutting operational efficiency and simplicity in their unitary construction. However, these saw blades leave room for improvement in their ability to protect adjacent soft tissue from exposure to the cutting action of the blades.

As such, there is a need for improved surgical saw blades which engage and cut bone in a smooth, stable, and efficient manner, while protecting the adjacent soft tissue from exposure to the cutting action of the saw blade.

Other references of interest may also include: U.S. Publication Nos. 2009/0093815 and 2009/0093814, the Applications of which are co-assigned and fully incorporated herein by reference; U.S. Publication Nos. 2008/0243125 and 2008/0027449; and U.S. Pat. Nos. 5,839,196, 5,439,472, 5,382, 249, 4,768,504, 4,617,930, and 1,726,241. U.S. Design patent Ser. No. 29/335,690, the contents of which are fully incorporated herein by reference, may also be of interest.

BRIEF SUMMARY OF THE INVENTION

Embodiments of the invention provide saw blade assemblies and systems using such saw blade assemblies which achieve safer, smoother, more reliable, more stable, and more efficient bone cutting. An exemplary saw blade assembly comprises an elongate monolithic blade, i.e., the elongate blade has a unitary construction with no moveably connected parts. The unitary construction of the elongate blade makes the saw blade assembly mechanically efficient. The elongate monolithic blade can be coupled to an oscillating drive member of a coupled drive unit and comprises proximal and distal ends. The elongate monolithic blade is driven in a small arc by the oscillating drive member from a center of oscillation or pivot point, at the proximal end. The distal end comprises a cutting edge which is shaped to engage or impact bone, or any target object, at a very shallow angle, reducing the occurrence of any disadvantageous bucking or "kicking." The saw blade assembly further comprises a sheath coupled to and partially enclosing the elongate monolithic blade. In use, the sheath is held stationary to protect adjacent soft tissue from exposure to the cutting action of the elongate blade while the elongate monolithic blade is driven.

In a first aspect, embodiments of the invention provide a saw blade assembly for use with a driver having an oscillatory drive member. The provided saw blade assembly can perform surgical cuts to bone tissue with minimal injury to surrounding tissue. The saw blade assembly comprises an elongate sheath and an elongate monolithic blade. The elongate sheath has a proximal end, a distal end, and an open interior. The proximal end of the elongate sheath is removably mountable on the driver to be held stationary relative to the driver when the saw blade assembly performs surgical cuts. The elongate monolithic blade is received within the open interior of the sheath. The monolithic blade has a central longitudinal axis, a proximal end, and a distal cutting end. The proximal end is pivotably mounted to the proximal end of the elongate sheath and removably couples to the oscillatory drive member of the driver when the proximal end of the elongate sheath is mounted on the driver. The distal cutting end is transverse to the central longitudinal axis and extends from the distal end of the sheath. To perform surgical cuts, the oscillatory drive shaft pivots the distal cutting end back and forth about a center of oscillation at the proximal end of the monolithic blade when the proximal end of the monolithic blade is coupled to the oscillatory drive member.

In many embodiments, the distal cutting end is configured to engage bone tissue at an angle of less than about 10 degrees. This angle may be less than about 6 degrees or even less than about 3 degrees.

In many embodiments, the saw blade assembly further comprises at least one elongate support rib. The at least one elongate support rib may be coupled to the elongate sheath or may be formed in the elongate sheath.

The distal cutting end of the monolithic blade is typically perpendicular to the central longitudinal axis of the monolithic blade.

The distal cutting end of the monolithic blade will typically comprise a plurality of teeth. Each tooth comprises a distal tip. The tips of each tooth may be positioned on a single straight line perpendicular to the central longitudinal axis of the elongate monolithic blade. Each tooth may be identically shaped. The plurality of teeth may comprise an even number of teeth.

In some embodiments, each tooth is shaped as a right triangle. Each tooth has a right angle, a hypotenuse opposite the right angle, and a longitudinal side adjacent the hypotenuse. The right angle of each tooth is oriented at least one of toward or away from the central longitudinal axis of the blade. The longitudinal side of each tooth may be disposed along a radial line extending from the tip of the tooth to the center of oscillation at the distal end of the monolithic blade. The longitudinal sides of each tooth may be parallel with one another. The right angle of each tooth may oriented away from the central longitudinal axis of the monolithic blade. The distal cutting end may further comprise a centrally positioned tooth shaped as an isosceles triangle. The centrally positioned tooth may be formed by two right triangular teeth sharing the same longitudinal side disposed along the central longitudinal axis of the blade.

In some embodiments, the tips of the plurality of teeth are disposed along an arc centered about the center of oscillation at the proximal end of the monolithic blade. In some embodiments, each tooth is identically shaped as an approximately isosceles triangle and the tips of the teeth are disposed along a lateral line perpendicular to the central longitudinal axis of the monolithic blade.

In some embodiments, the plurality of teeth comprises a plurality of inner teeth and a plurality of outer teeth. The tips of the inner teeth may be disposed on a first single straight line perpendicular to the central longitudinal axis. The tips of the outer teeth may be disposed on a second single straight line perpendicular to the central longitudinal axis, the first single straight line being different than the second single straight line.

In many embodiments, at least a portion of the monolithic blade comprises at least one of metal, stainless steel, composite, carbon fiber composite, polymer, titanium, or ceramic.

Embodiments of the invention also provide a surgical saw system for performing surgical cuts to bone tissue with minimal injury to surrounding tissue. The surgical saw system comprises the above described saw blade assembly and a driver assembly. The drive assembly comprises the driver having the oscillatory drive member. The drive assembly is configured to couple to the saw blade assembly to pivotably drive the monolithic blade of the saw blade assembly to cut tissue.

In many embodiments, the surgical saw system further comprises an external battery pack coupleable to the drive assembly to power the drive assembly.

In many embodiments, the drive assembly is hand-holdable.

In many embodiments, the drive assembly comprises a locking mechanism having an open configuration and a closed configuration. The saw blade assembly is insertable into the locking mechanism in the open configuration to couple the saw blade assembly to the drive assembly. The locking mechanism in the closed configuration holds the sheath of the saw blade assembly stationary relative to the driver and couples to the elongate monolithic blade when the drive assembly is coupled to the saw blade assembly. The locking mechanism may comprise a lever actuatable to switch the locking mechanism between the open and closed configurations. The near end of the monolithic blade may define an aperture at the center of oscillation The linkage mechanism may comprise a knob which fits into the aperture of the near end of the monolithic blade when the linkage mechanism is in the closed configuration when the drive assembly is coupled to the saw blade assembly. The locking mechanism may comprise a sleeve slot adapted to hold the near end of the sleeve stationary relative to the driver when the saw blade assembly is inserted into the locking mechanism.

In many embodiments, the oscillatory drive member comprises a blade slot adapted to hold the near end of the monolithic blade when the saw blade assembly is inserted into the locking mechanism.

In many embodiments, the drive assembly comprises an electric motor and an eccentric mechanism coupled to the electric motor. The eccentric mechanism may be coupled to the oscillatory drive member to oscillate the blade about its center of oscillation when the saw blade assembly is coupled to the drive assembly. The drive assembly may further comprise a trigger pressable to activate the electric motor. The electric motor may be removable from the drive assembly.

In many embodiments, the surgical saw system further comprises a noise absorbent sheath for covering at least a portion of the drive assembly.

In many embodiments the surgical saw system further comprises at least one cutting guide configured to guide the saw blade assembly in cutting bone tissue.

Embodiments of the invention also provide a method for performing surgical cuts to bone tissue with minimal injury to surrounding tissue. The saw blade assembly as described above is provided. The saw blade assembly is engaged with the oscillatory drive member. The saw blade assembly is positioned at a target site. To cut tissue at the target site with the far cutting end of the monolithic blade of the saw blade assembly, movement that is atraumatic to surrounding tissue is produced.

To engage the saw blade assembly with the oscillatory drive member, the near end of the monolithic blade may be inserted into a blade slot of the oscillatory drive member. When the saw blade assembly is engaged with the oscillator drive member, the near end of the sheath of the saw blade assembly may be held stationary with a locking mechanism of the driver. To cut tissue at the target site, the blade of the saw blade assembly may be pivoted back and forth about the center of oscillation at the near end of the blade. The movement of the cutting surface may be constrained within one plane. The tissue site may be an orthopedic site, a bone, a vertebrae or a skull. The distal cutting end of the blade may be positioned within a tissue structure while movement of the remainder of the blade member does not cause hemorrhage of a vascular network of the structure.

The method may further comprise the utilization of a channel in at least a portion of the saw blade assembly to view, aspirate or irrigate the tissue site.

In another aspect, embodiments of the invention provide a method for surgical cutting of bone. The bone is contacted with a distal cutting edge of an elongate monolithic blade. The distal end comprises a plurality of teeth. Each tooth ends in a distal tip. The distal tips of the teeth are positioned on a line perpendicular to the central longitudinal axis of the elongate monolithic blade such that said teeth provide better tracking of the elongate monolithic blade when forming a kerf in the bone. The bone is cut by oscillating the distal cutting edge in a small arc about a center of oscillation at a proximal end of the elongate monolithic blade to form the kerf. The tissue surrounding the bone is shielded from the movement of the portion of the elongate monolithic blade proximal to the distal cutting end with an elongate sheath enclosing said portion of the elongate monolithic blade. The teeth can cut both progressively and sequentially as the kerf begins to form into a v-shape to provide stable, accurate, aggressive cutting and efficient chip removal.

BRIEF DESCRIPTION OF THE DRAWINGS

FIG. 1A shows a known surgical saw blade assembly having a plurality of linked gears;

FIG. 1B shows a known surgical saw blade assembly having a pair of reciprocating push rods;

FIG. 5I1 shows a front view of an elongate blade of a surgical saw blade assembly according to embodiments of the invention;

FIG. 5I2 shows a magnified view of the distal cutting edge of FIG. 5I1;

DETAILED DESCRIPTION OF THE INVENTION

Figure 2A:
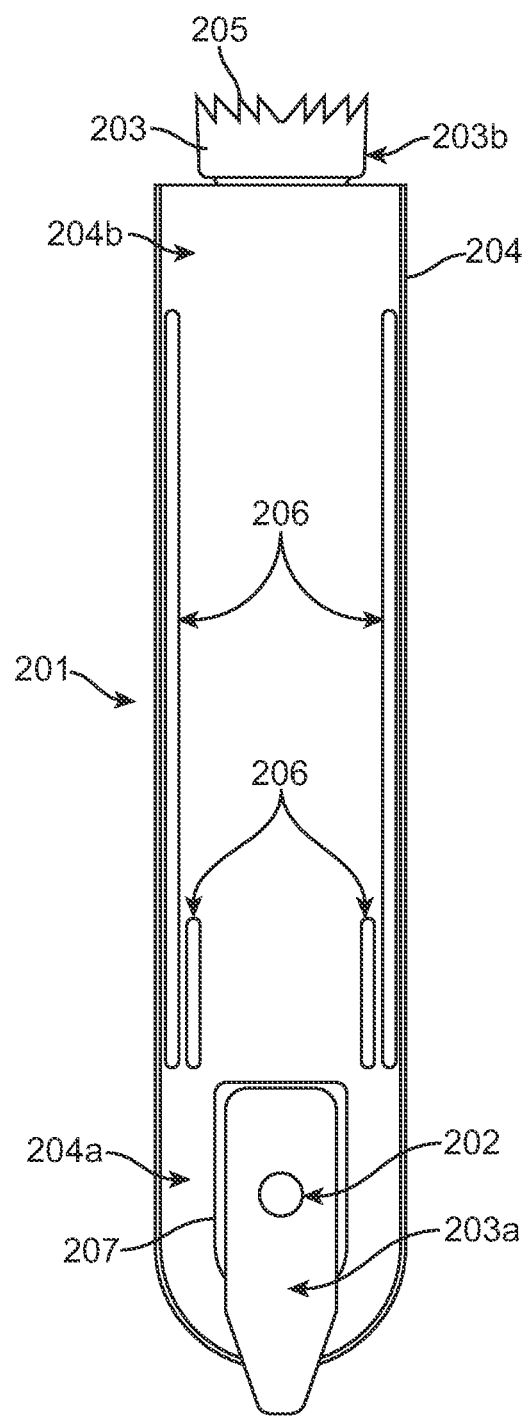
FIG. 2A shows a front view of a surgical saw blade assembly according to embodiments of the invention.
Figure 2B:
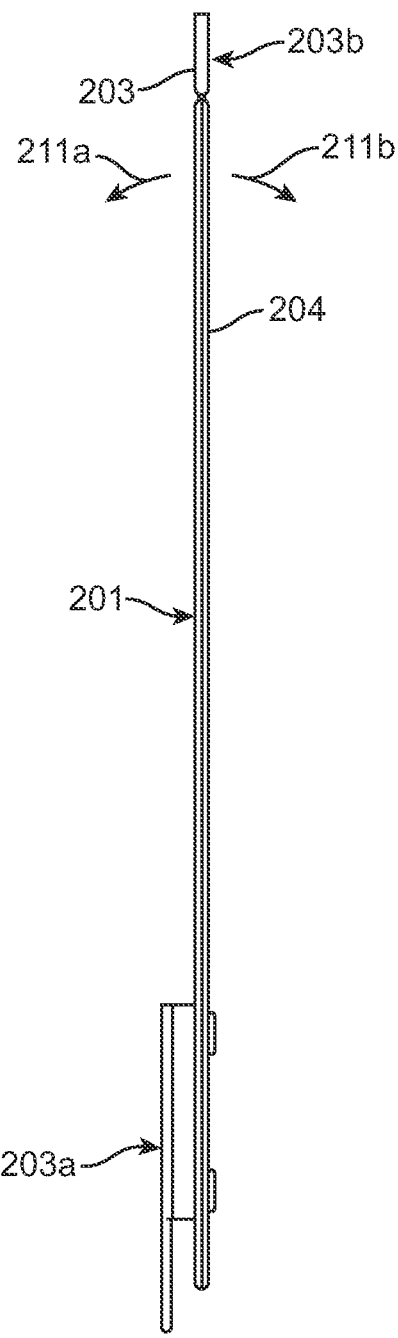
FIG. 2B shows a side view of the surgical saw blade assembly of FIG. 2A.
Figure 2C:
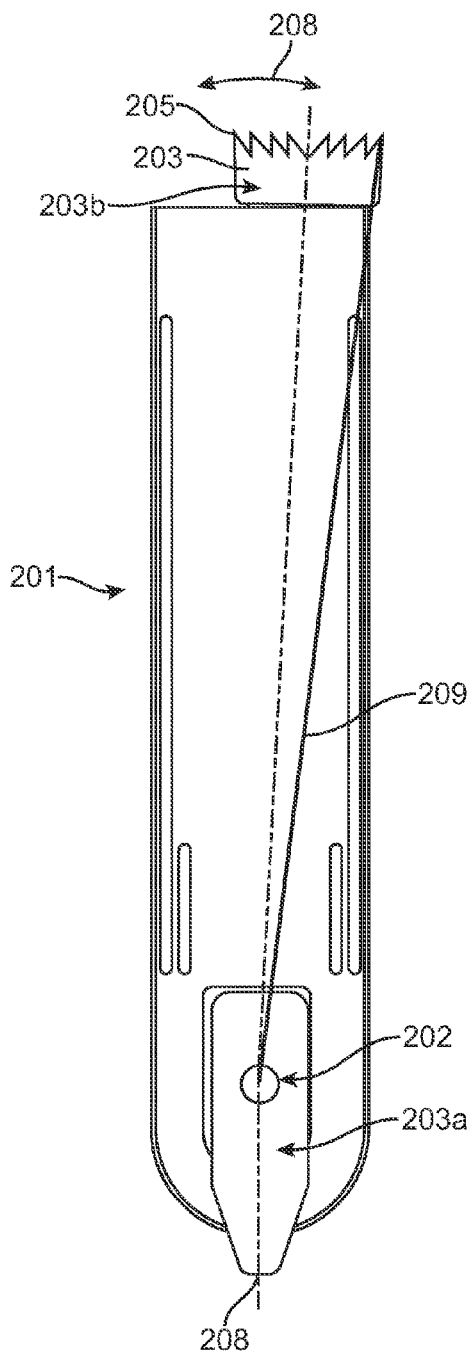
FIG. 2C shows a front view of the surgical saw blade assembly of FIG. 2A with its distal cutting end pivoted to the right.
Figure 2D:
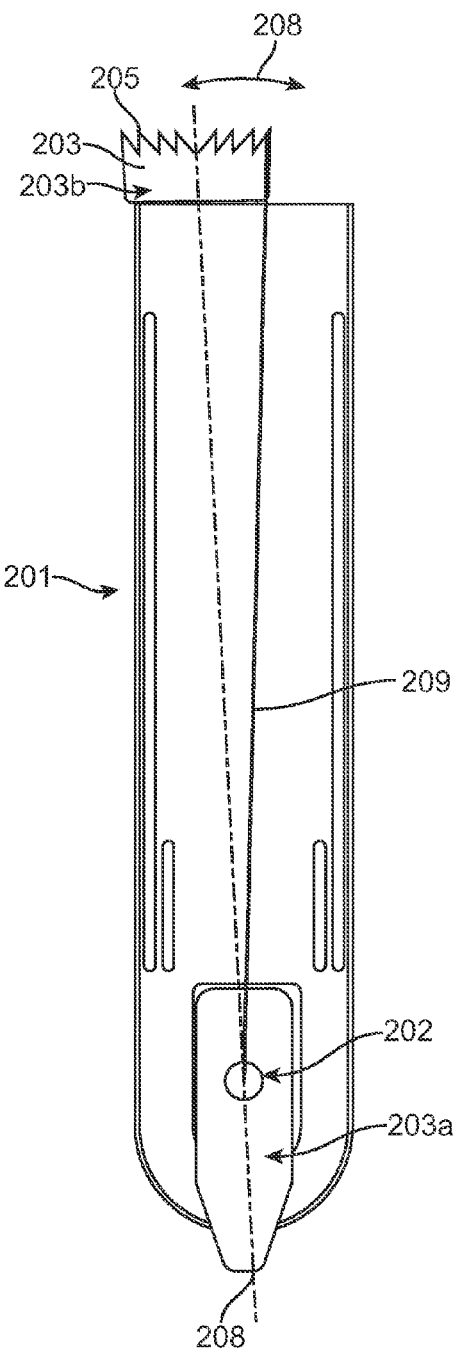
FIG. 2D shows a front view of the surgical saw blade assembly of FIG. 2A with its distal cutting end pivoted to the left.

FIGS. 2A and 2B respectively show front and side views of a saw blade assembly 201 according to embodiments of the invention. The saw blade assembly 201 comprises an elongate monolithic blade 203 and an elongate sheath 204. The elongate monolithic blade 203 has a unitary construction with no moveably connected parts, making it much more mechanically efficient than known surgical saw blades employing translation mechanisms with moveably connected moving internal parts. Typically, the majority of the elongate monolithic blade 203 is housed within the interior of the elongate sheath 204. The elongate sheath 204 will typically have no other moving internal parts besides the elongate monolithic blade 203. The elongate monolithic blade 203 has a proximal end 203a and a distal cutting end 203b comprising a cutting edge 205 which typically comprises a plurality of sharp projections or teeth. The elongate sheath 204 has a proximal end 204a and a distal end 204b, which as shown in FIGS. 2A and 2B, may be U-shaped. The elongate sheath 204 further defines an aperture 207 from where the proximal end 203a of the elongate monolithic blade 203 extends through. As shown in FIGS. 2C and 2D, when coupled to and driven by a drive source at the proximal end 203a, the elongate monolithic blade 203 oscillates in a small arc 208 about a center of oscillation or pivot point 202 at the proximal end 203a. The distal cutting end 203a of the elongate monolithic blade 203 extends out of the distal end 204b of the elongate sheath 204 to cut tissue. Because the remainder of the body of the elongate monolithic blade 203 is enveloped by the elongate sheath 204, tissue is only exposed to the high-speed lateral motion of the distal cutting end 203b.

In some embodiments, the saw blade assembly 201 may be lubricated to reduce friction. A lubricous material or coating may be provided for the elongate monolithic blade 203 and/or the elongate sheath 204. For example, the exterior surface of the elongate monolithic blade 203 and/or at least the internal surface of the elongate sheath 204 may be coated with a lubricous substance, for example; composite diamond, thermal plasma sprayed ceramic, zirconia nitride, titanium-carbo nitride, titanium nitride, titanium oxide, chromium oxide, or the surfaces of the monolithic blade 203 and/or the elongate sheath 204 may be subject to plasma or ion nitriding, inducing a lubricious conversion layer upon them.

In some embodiments, the elongate sheath 204 comprises at least one elongate support member 206. As shown in FIG. 2A, the elongate sheath 204 comprises four elongate support member 206, two for each side of the elongate sheath 204, the two comprising one long support member and one short support member. An elongate support member 206 may comprise an external member or bar attached to the elongate sheath 204, for example, by welding. An elongate support member 206 may be formed in the elongate sheath 204, for example, as an indented region. In many embodiments, the saw blade assembly 201 can be longitudinally flexed and bent, as indicated by arrows 211a and 221b, without significantly or adversely affecting the oscillating cutting motion of the elongate monolithic blade 203.

As shown in FIGS. 2A and 2B, the cutting edge 205 is disposed at the distal most portion of the distal cutting end 203b. The cutting edge 205 may alternatively be placed at other locations along the distal cutting end 203b. The cutting edge 205 typically comprises a plurality of sharp projections or teeth but may alternatively comprise a single sharp edge or a combination of an edge or teeth (e.g., similar to a serrated knife). The teeth of the cutting edge 205 can be hardened relative to the remainder of the elongate monolithic blade 203 to improve their ability to cut bone. Also, the hardness, pitch and dimensions of the teeth can be selected for the particular bone tissue to be cut, for example, femoral, tibial, hip, spinal, cranial, dental mandibular, and/or other bone tissue. Smaller teeth and pitch can be used for finer cuts in, for example, spinal tissue, whereas larger teeth and pitch can be used for cuts to the distal or proximal femur or tibia. For example, the teeth may have a finer pitch in the central portion of the blade and a coarser pitch along the edges of the blade.

The saw blade assembly 201, including elongate monolithic blade 203 and the elongate sheath 204, can be fabricated from a number of or a matrix of surgical grade metals, alloys, ceramics, cera-metallic composites or other composites known in the art. Preferably, at least the distal cutting end 203b of the elongate monolithic blade 203 comprises surgical grade stainless steel, for example, hardened and tempered stainless steel. Forging, machining, laser cutting, stamping, grinding, and/or other known metal fabrication methods may be used to fabricate an elongate monolithic blade 203 and an elongate sheath 204 comprising metal. The elongate monolithic blade 203 and/or the elongate sheath 204 can also be treated or processed using one or more known metal treatment methods. The specific material for the elongate monolithic blade 203 and the elongate sheath can be selected based on one or more properties including elastic modulus, elastic limit, tensile strength, yield strength, compressive strength, resonance frequencies, lubricity, coefficient of friction, and hardness.

In some embodiments, the saw blade assembly may be manufactured so that different portions of the saw blade assembly have different material properties. For example, the distal and proximal portions of the saw blade assembly can be fabricated from harder materials while the middle portion of the saw blade assembly can be fabricated from more flexible materials. This may allow the saw blade assembly to better bend and flex longitudinally while maintaining the material property requirements of the cutting edge 205. Alternatively or in combination, different portions of the saw blade assembly may be treated using different known metallurgical treatments such as annealing, tempering, nitriding, stress relieving, work hardening, and surface treatment and/or coating.

Figures 3A, 3B:
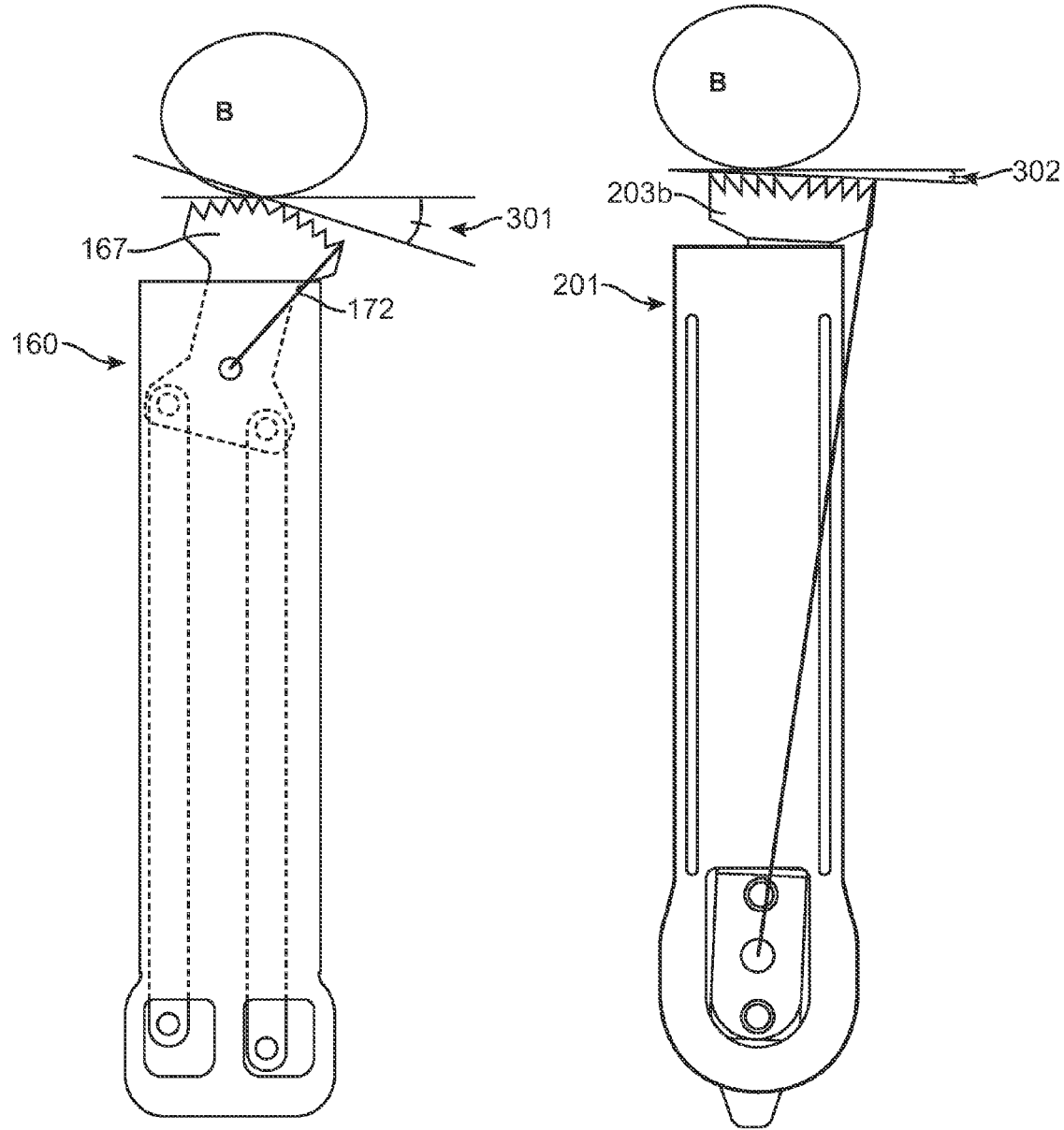
FIG. 3A shows the known surgical saw blade assembly of FIG. 1B engaging bone.
FIG. 3B shows the known surgical saw blade assembly of FIG. 2A engaging bone.

FIG. 2C again shows a front view of the surgical saw blade assembly 201, this time with the distal cutting end 203b pivoted toward to its right-most lateral position. FIG. 2D shows a front view of the surgical saw blade assembly with the distal cutting end 203b pivoted toward its left-most lateral position. The elongate monolithic blade 203 defines a central longitudinal axis as shown by dotted line 208. The central longitudinal axis 208 separates the elongate monolithic blade 203 into two lateral sides. Typically, the central longitudinal axis 208 extends from the center of oscillation 202 to the middle of the cutting edge 205. As previously discussed, when coupled to and driven by a drive source at the proximal end 203a, the elongate monolithic blade 203 oscillates in a small arc 208 about a center of oscillation or pivot point 202 at the proximal end 203a. The pivot radius 209 of the elongate monolithic blade 203 thus extends from the proximally disposed center of oscillation 202 to the distal tips of the teeth of the cutting edge 205. Thus, the pivot radius 209 of the elongate monolithic blade 203 is much longer than those of known surgical saw assemblies, for example, the pivot radius 122 of known saw blade assembly 110 shown in FIG. 1A and the pivot radius 172 of known saw blade assembly 160 shown in FIG. 1B. Because the pivot radius 209 is much longer, the cutting edge 205 engages or impacts bone or any target object at an angle much shallower than that of known saw blade assemblies which instead have distally disposed centers of oscillation. This is shown by FIGS. 3A and 3B which shows the impact angles of the known saw blade assembly 160 and the saw blade assembly 201, respectively. As shown in FIG. 3A, because of the shorter pivot radius 172, the distal toothed cutting member 167 impacts bone B at a sharp angle 301, for example, an angle of about 13.5 degrees or greater, as it oscillates. As shown in FIG. 3B, because of the longer pivot radius 209, the distal cutting end 203b impacts bone B at a shallower angle 302 as it oscillates. The elongate monolithic blade 203 will typically be configured so that the shallow angle 302 comprises an angle of less than about 10 degrees, preferably an angle of less than about 6 degrees, and more preferably an angle of less than about 3 degrees.

Figure 4A:
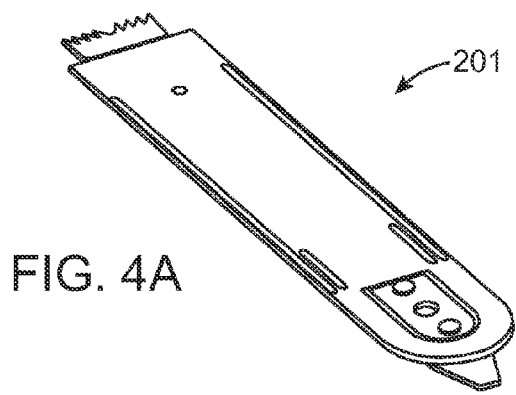
FIG. 4A shows a perspective view of the surgical saw blade assembly of FIG. 2A.
Figure 4B:
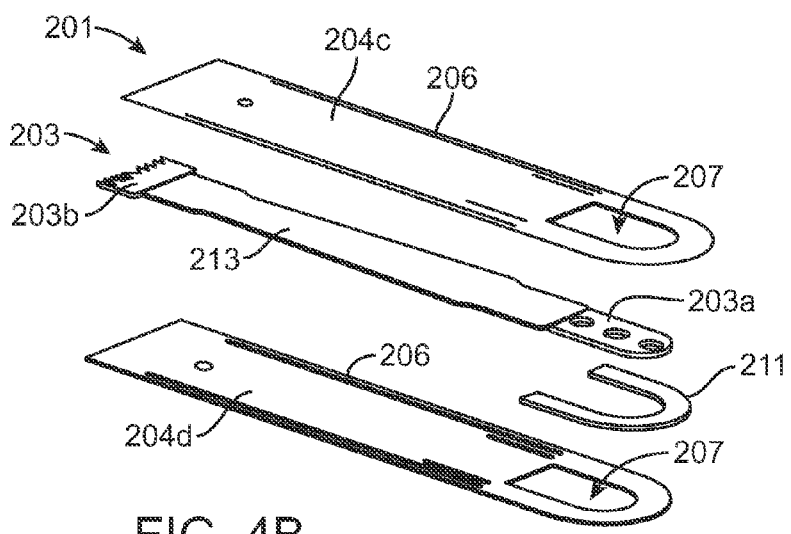
FIG. 4B shows an exploded view of the surgical saw blade assembly of FIG. 2A.

FIG. 4A shows a perspective view of the surgical saw blade assembly 201. FIG. 4B shows an exploded view of the surgical saw blade assembly of 201. The elongate sheath 204 comprises a first elongate sleeve portion 204c, which may be a top portion, and a second elongate sleeve portion 204d, which may be a bottom portion. The aperture 207 is present on both the first elongate sleeve portion 204c and the second elongate sleeve portion 204d. A spacer 211 may be disposed between the first elongate sleeve portion 204c and the second elongate sleeve portion 204d at their proximal ends. The elongate monolithic blade 203 may comprise a main blade body 213 and a drive unit coupling member 212 fixedly coupled to a main body 213. At least a portion of the drive unit coupling member 212 will be thicker than and/or have an area greater than that of the aperture 207. Thus, when the first elongate sleeve portion 204c, the main blade body 213, the spacer 211, the second elongate sleeve portion 204d, and the drive unit coupling member 212 are brought together and attached to form the surgical saw blade assembly 201, the main blade body 213 is prevented from sliding out of the elongate sheath 204 and is also pivotable within the elongate sheath 204, even without attachment to a drive unit. In some embodiments, the drive unit coupling member 212 is integral with the main body 213, and the elongate sheath 204 comprises more than two elongate sleeve portions which are built around the elongate monolithic blade 203.

The surgical saw blade assembly 201 may further comprise elongate support members 206. The first elongate sleeve portion 204c and the second elongate sleeve portion 204d may have complimentary support members 206. The support members 206 may comprise an external member or bar attached to at least one of the first elongate sleeve portion 204c or the second elongate sleeve portion 204d, for example by welding. Alternatively or in combination, the support members 206 may be formed by indentations in the respective sleeve portions. Complimentary support members 206 may be lap-welded or spot-welded together to make the elongate sheath 204 more structurally rigid.

Figure 4C:
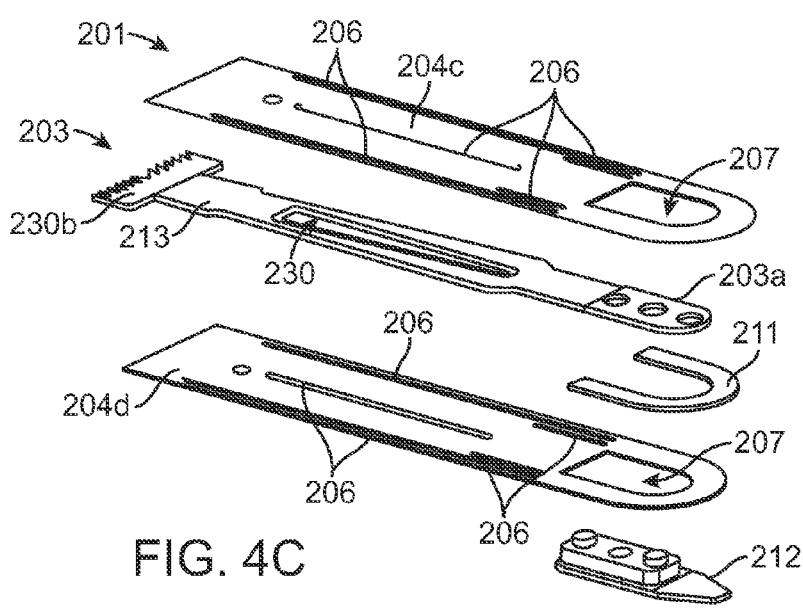
FIG. 4C shows an exploded view of a surgical saw blade assembly according to an embodiment of the invention.

In some embodiments, for example, as shown in FIG. 4C, the main body 213 may have a central aperture 230. Having a central aperture 230 can, among other things, lighten the main body 213 as well as provide clearance for a centrally disposed elongate support member 206. The centrally disposed elongate support member 206 may comprise an internal bar attached to at least one of the first elongate sleeve portion 204c or the second elongate sleeve portion 204d, for example, by welding.

Figure 4D:
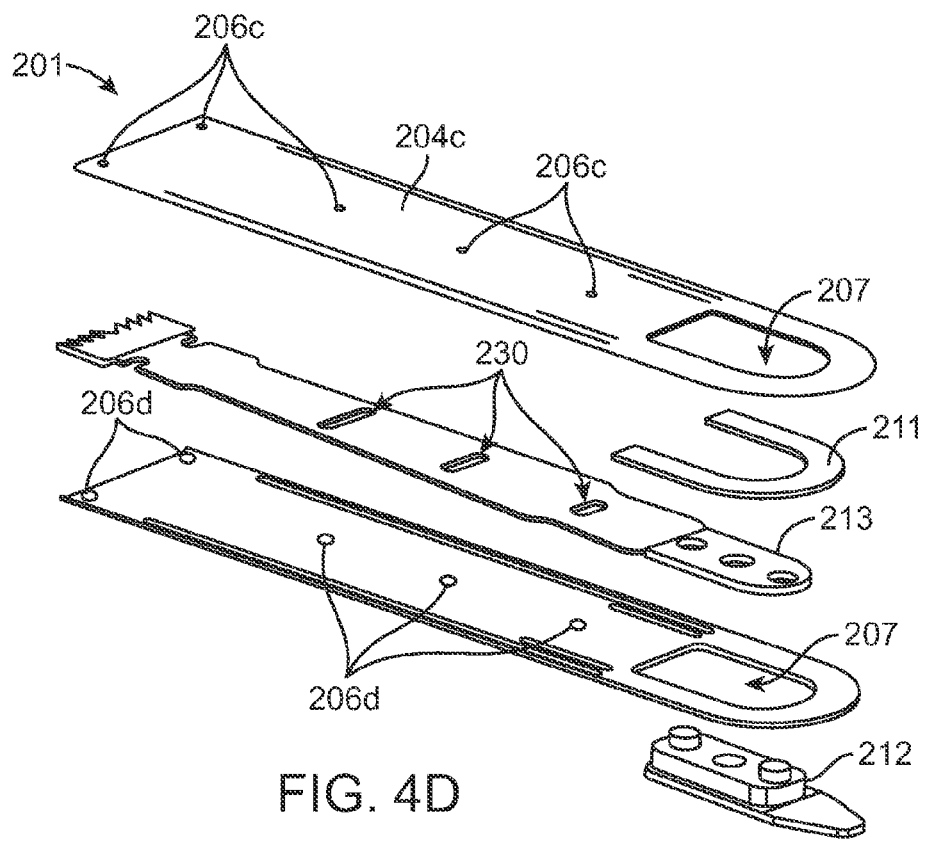
FIG. 4D shows an exploded view of a surgical saw blade assembly according to another embodiment of the invention.

Alternatively or in combination, the support members 206 may comprise complimentary first elongate sleeve portion indentations 206c and second elongate sleeve portion indentations 206d, for example, as shown in FIG. 4D. Complimentary indentations 206c, 206d may be attached together, for example, by welding, lap-welding, spot-welding, brazing, soldering, etc., to make the elongate sheath 204 more structurally rigid. As shown in FIG. 4D, there may be more than one centrally disposed elongate support member 206 and the main body 213 of the elongate monolithic blade 203 may have more than one central aperture 230, each central aperture 230 corresponding to and straddling their respective centrally disposed support member 206.

Figure 4E:
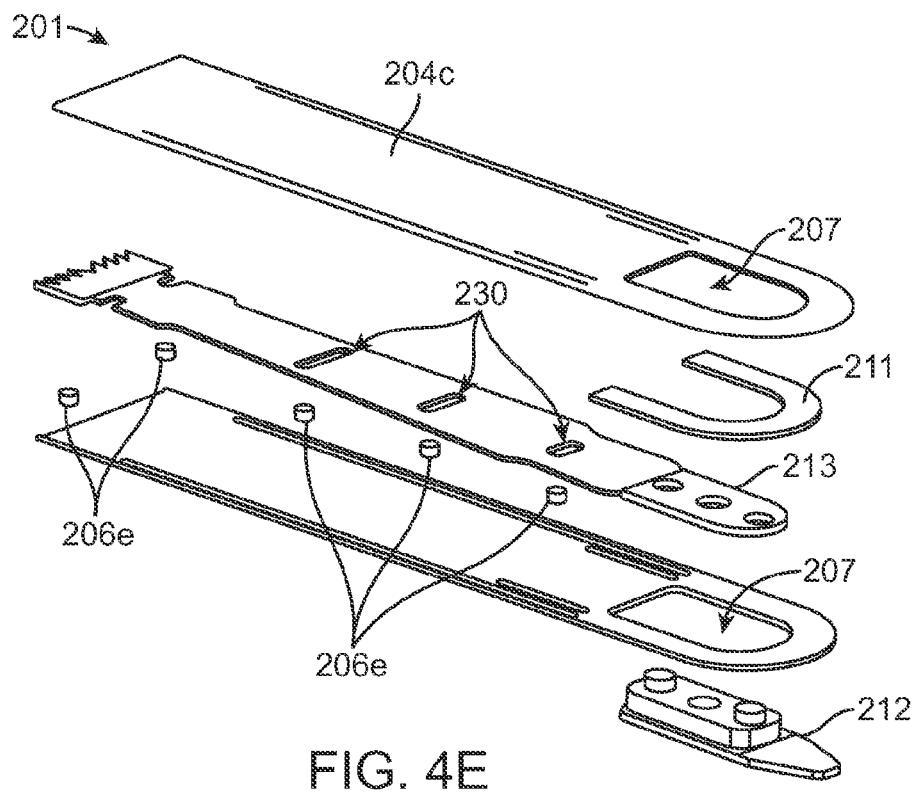
FIG. 4E shows an exploded view of a surgical saw blade assembly according to yet another embodiment of the invention.

Alternatively or in combination, the surgical saw blade assembly 201 may comprise a plurality of discrete support members 206e which are attached to the first elongate sleeve portion 204c and the second elongate sleeve portion 204d, for example, as shown in FIG. 4D. The discrete support members 206e may be attached together, for example, by welding, spot-welding, brazing, soldering, etc., to make the elongate sheath 204 more structurally rigid. As shown in FIG. 4E, there may be more than one centrally disposed elongate support member 206e and the main body 213 of the elongate monolithic blade 203 may have more than one central aperture 230, each central aperture 230 corresponding to and straddling their respective centrally disposed support member 206.

The distal cutting end 203b of the elongate monolithic blade 203 can have many configurations. FIGS. 5A to 5H show exemplary distal cutting ends 203b.

In many embodiments, the cutting edge 205 may be similar to the cutting edges described in co-assigned U.S. Pat. Nos. 6,022,353, 6,503,253, 6,723,101, and 7,527,628 and U.S. Publication Nos. 2009/0093815, 2009/0093814.

The cutting edge 205 can comprise a plurality of teeth. Different toothed cutting edges 205 can have different numbers of teeth. For example, as shown in FIGS. 2A, 2C, 3B, 4A, 4B and 5A, the cutting edge 205a can have a total of eight teeth, with four teeth on each side of the central longitudinal axis 209 of elongate monolithic blade 203. As shown in FIG. 5B, the cutting edge 205b can have a total of six teeth, with three teeth on each side of central longitudinal axis 209 of elongate monolithic blade 203. As shown in FIG. 5C, the cutting edge 205c can have a total of twelve teeth, with six teeth on each side of central longitudinal axis 209 of elongate monolithic blade 203. As shown in FIG. 5D, the cutting edge 205d can have a total of ten teeth, with five teeth on each side of central longitudinal axis 209 of elongate monolithic blade 203. Also as shown in FIG. 5D, the proximal edges 216 of the distal cutting end 203b can be angled. As shown in FIG. 5E, the cutting edge 205e can have a total of sixteen eight teeth, with eight teeth on each side of central longitudinal axis 209 of elongate monolithic blade 203 and with pairs of teeth flaring from a common central member, forming the shape of a "whale tale." As shown in FIG. 5F, the cutting edge 205f can have a total of twelve teeth, with six teeth on each side of central longitudinal axis 209 of elongate monolithic blade 203, each tooth being shaped as an isosceles triangle. As shown in FIG. 5G, the cutting edge 205g can have a total of six teeth, with three teeth on each side of central longitudinal axis 209 of elongate monolithic blade 203 and a central void. As shown in FIG. 5H, the cutting edge 205h can have a total of seven teeth, with three teeth on each side of central longitudinal axis 209 of elongate monolithic blade 203 and one central tooth. Any number and/or arrangement of teeth may be used. The distal cutting ends 203b have varying levels of width, depending on the requirement of a surgeon or of a specific procedure.

In some embodiments, for example, as shown in FIG. 5F, the tips of the teeth form an arc 515 coinciding with the arc of travel of the blade. More preferably, however, many embodiments of the invention have the tips of the teeth forming a single straight line 510, for example, as shown in FIGS. 5A, 5B, 5C, 5D, 5E, 5G and 5H, i.e., the teeth are arranged in a "flat-top" pattern. Preferably, the straight line 510 is perpendicular to the central longitudinal axis 209 of the elongate monolithic blade. Having the teeth arranged in a "flat-top" pattern causes each tooth to progressively cut more material than the previous tooth as explained in more detail below.

Collectively, all teeth contact the bone to be cut make progressive contributions. As the distal cutting end having its teeth in a "flat-top" pattern delves more deeply into the bone, the teeth on one end of the cutting edge may contact bone while the teeth on the opposite end are pulled away from the bone, making bone chip evacuation much more efficient and reducing friction and thus the operating temperature of the distal cutting end. Having the teeth in a "flat-top" pattern also contributes to the shallow impact angle of the distal cutting end 203b as explained in detail below. Cutting with teeth in a "flat-top" pattern forming a straight line 510 substantially perpendicular to the central longitudinal axis 209 of the elongate monolithic blade 203 generally results in a shallow convex or "v-shaped" kerf when engaging and cutting bone. When the distal cutting end having its teeth in an "arc" pattern delves more deeply into the bone, each of the teeth may contact bone tissue, increasing friction and thus the operating temperature of the distal cutting end and making bone chip evacuation much less efficient. Cutting teeth in an "arc" pattern generally results in a convex-shaped kerf being when engaging and cutting bone.

Figure 5A:
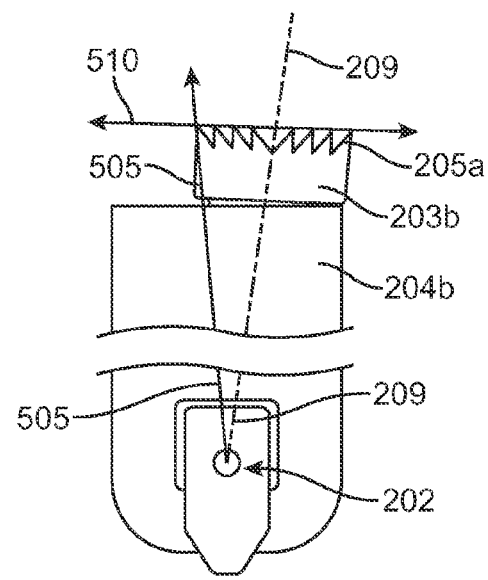
FIGS. 5A to 5H show distal cutting edges of surgical saw blade assemblies according to embodiments of the invention.
Figure 5B:
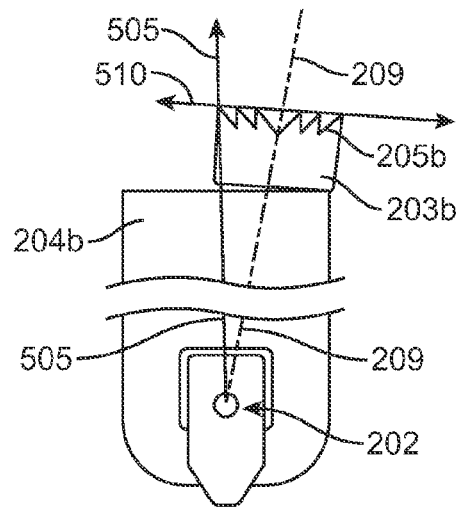
Figure 5C:
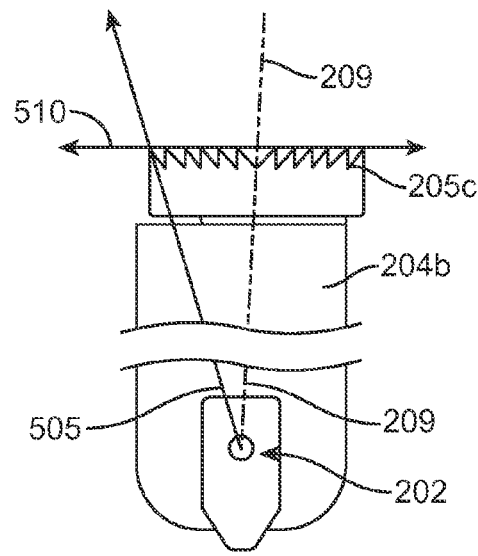
Figure 5D:
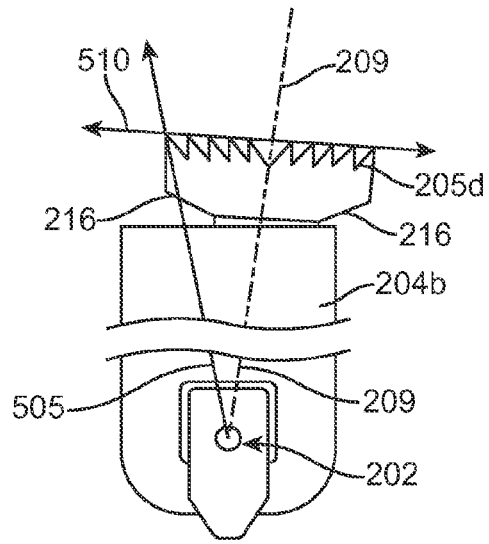
Figure 5E:
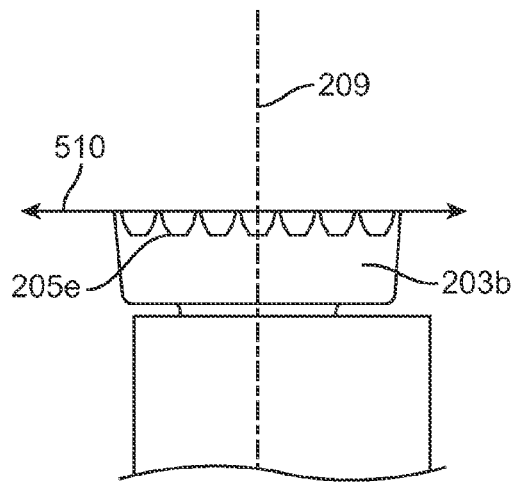
Figure 5F:
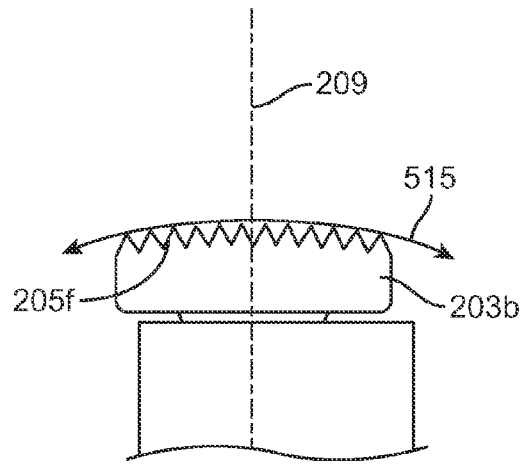
Figure 5G:
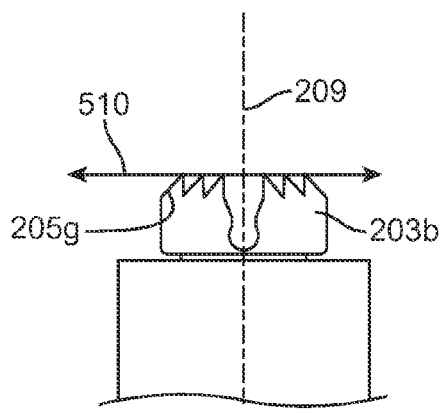
Figure 5H:
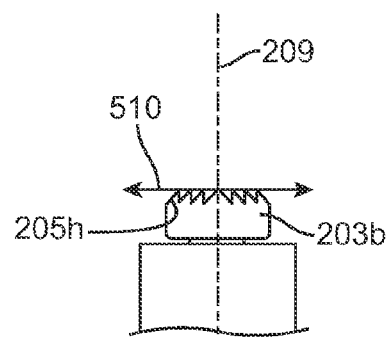

As shown in FIGS. 5A, 5B, 5C, 5D, 5G, 5H, 5I1, and 5I2, the teeth of the cutting edge 205 (including cutting edge 205a, cutting edge 205b, cutting edge 205c, cutting edge 205d, cutting edge 205e, cutting edge, 205g, and cutting edge 205h, and cutting edge 205i) can be shaped as right triangles. For example, FIG. 5I1 shows an elongate monolithic blade 203 having a cutting edge 205 with a total of twelve teeth, with six teeth on each side of central longitudinal axis 209 of elongate monolithic blade 203. FIG. 5I2 shows a magnified view of the distal cutting end 203b and the cutting edge 205 of FIG. 5I1. As shown, for example, by FIG. 5I2, each tooth 220 has a free longitudinal side 245, a right angle 240, a hypotenuse 235 opposite the right angle 240, and a distal tip 235. The cutting occurs on the tip of the teeth.

As shown in FIGS. 5A, 5B, 5C, 5D, 5I1, and 5I2, the teeth of the cutting edge 205 (including cutting edge 205a, cutting edge 205b, cutting edge 205c, cutting edge 205d, and cutting edge 205i) may be oriented so that their right angles and hypotenuses face toward the central longitudinal axis 209 of the elongate monolithic blade 203. As shown in FIGS. 5G and 5H, the teeth of the toothed cutting edge 205 (including cutting edge 205g and cutting edge 205h) may alternatively be oriented so that their right angles and hypotenuses face away from the central longitudinal axis 209 of the elongate monolithic blade 203. In some embodiments, for example, as shown by FIG. 5E, the teeth of the toothed cutting edge 205 may comprise some teeth that have their right angles and hypotenuses facing toward the central longitudinal axis 209 and other teeth that have their right angles and hypotenuses facing away from the central longitudinal axis 209. In some embodiments, the right triangles of the teeth may be "near" right angles with the included angle greater than 90 degrees for a more aggressive cut.

Figure 5J:
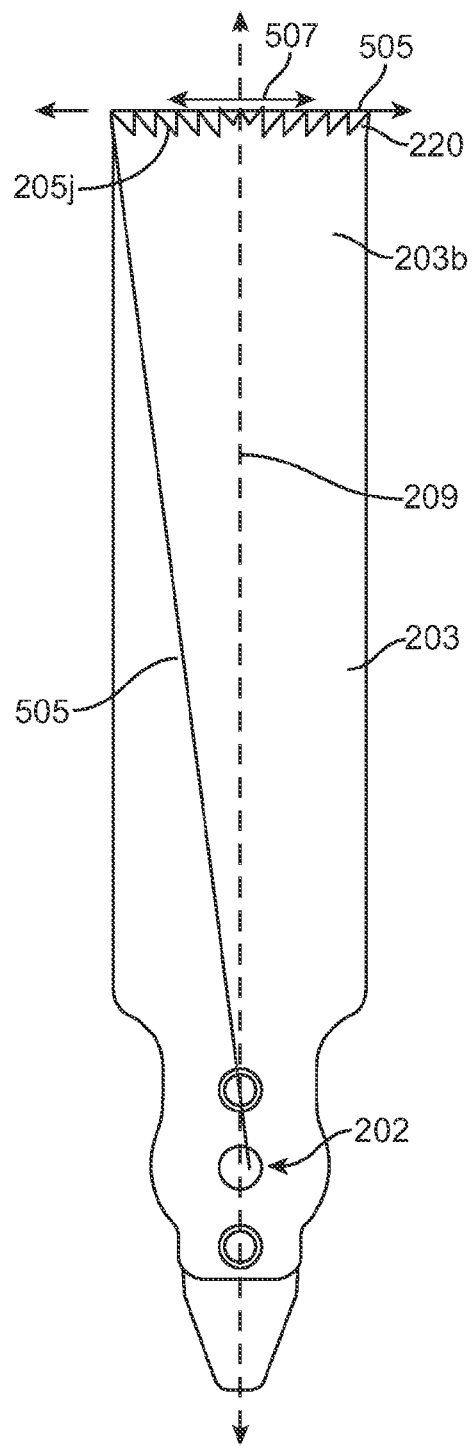
FIG. 5J shows an elongate blade of a surgical saw blade assembly according to embodiments of the invention.

FIG. 5J shows an elongate monolithic blade 203 according to another embodiment of the invention. The distal cutting edge 205j of the elongate monolithic blade 203 comprises a plurality of teeth 220. The distal cutting edge 205j has an odd number of teeth 220, with a central isosceles shaped tooth. The central isosceles shaped tooth and its laterally adjacent teeth, which are shaped as right triangles with their hypotenuses facing toward the central longitudinal axis 209, are positioned forward relative to the remainder of the teeth, which are shaped as right triangles with their hypotenuses facing toward the central longitudinal axis 209. The tips of the remainder of the teeth, i.e., the outer teeth, are disposed on a line 505 perpendicular to the central elongate axis 209. The tips of the central isosceles shaped tooth and its laterally adjacent teeth are disposed on a line 507 perpendicular to the central elongate axis 209 and forward of the line 505.

Each of the triangular teeth of the distal cutting edge 205 may have approximately the same size and/or shape. In the distal cutting edge 205, the central isosceles triangular tooth may comprise two right angled teeth sharing the same longitudinal side. In many embodiments, the triangular teeth of the distal cutting edge 205 may have a size and shape slightly different from one another. For example, in the embodiments of FIGS. 5A, 5B, 5C and 5D, the longitudinal side of each tooth may coincide with their respective radial line 505 extending from the center of oscillation 202 to the distal tip of the same tooth. Likewise, in the embodiment of FIGS. 5I1 and 5I2, the longitudinal side of each right triangular tooth may coincide with its respective radial line 505 extending from the center of oscillation 202 to the distal tip of the same tooth. Thus, the right angles 240 of each tooth face toward the central longitudinal axis 209 at slightly different angles, causing each tooth to have a slightly different size and shape from one another. The longitudinal sides of the teeth of the distal cutting edge 205 of FIG. 5H may also be similarly configured (that is, to have the longitudinal sides of each tooth coincide with each tooth's radial line 505) to have the right angles of each tooth face away from the central longitudinal axis 209 at slightly different angles.

Figure 6B:
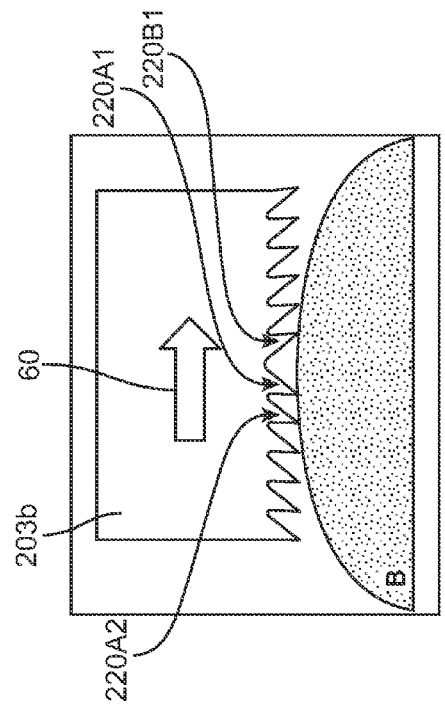
FIGS. 6A to 6U show a distal cutting edge engaging and cutting bone according to embodiments of the invention.
Figure 6D:
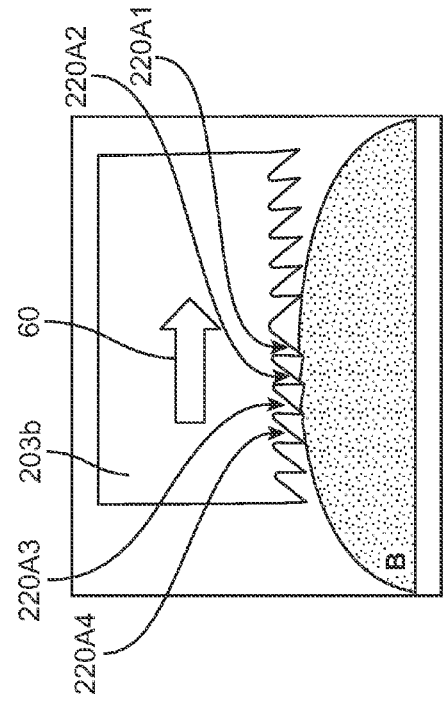
Figure 6A:
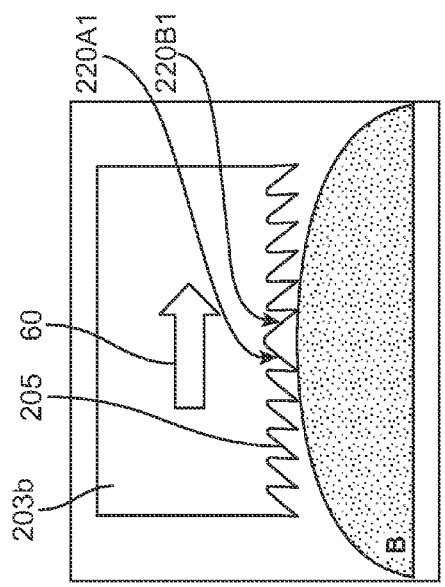
Figure 6C:
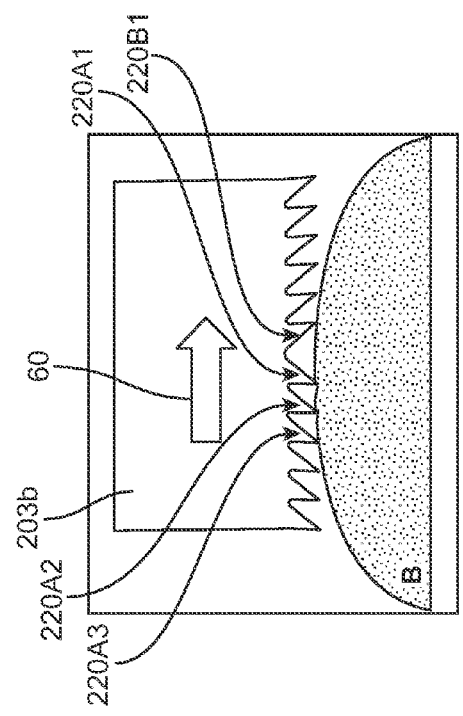
Figure 6M:
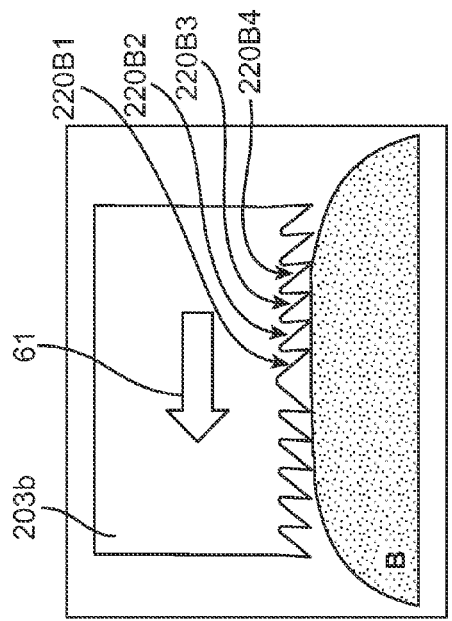
Figure 6N:
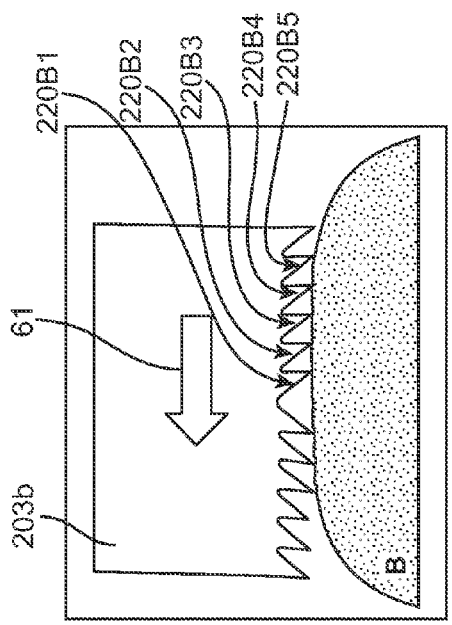
Figure 6O:
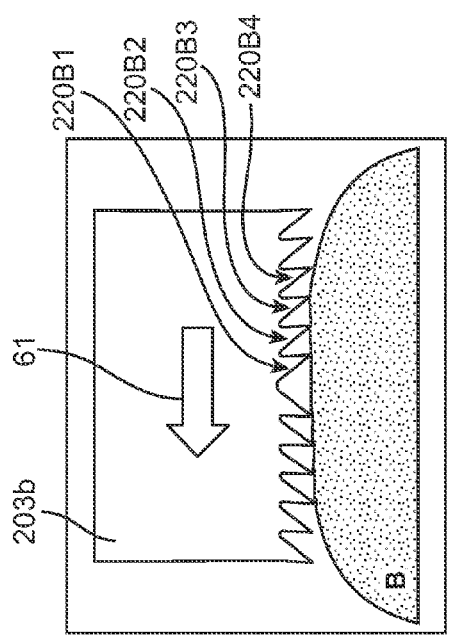
Figure 6P:
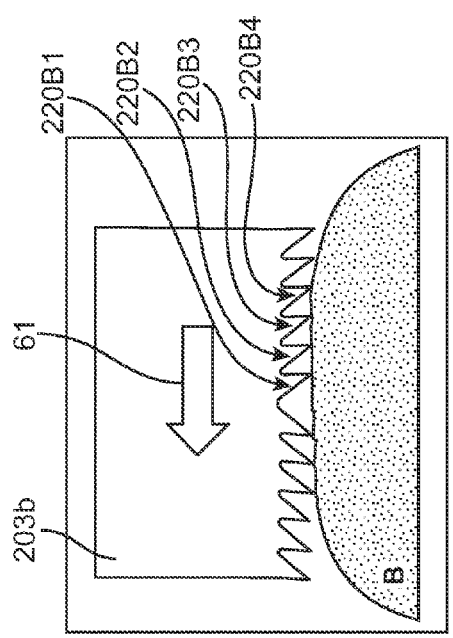
Figure 6U:
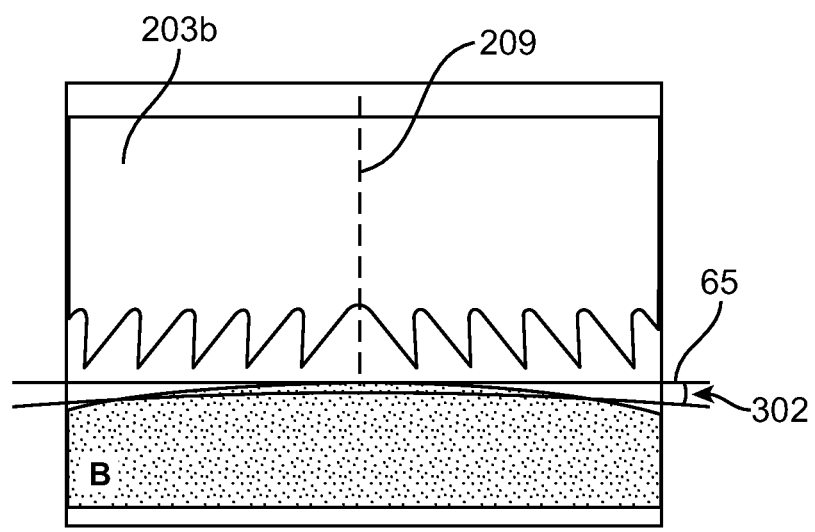

FIGS. 6A to 6U show the distal cutting edge 203b as it engages and cuts bone tissue B through a cycle of oscillation. In the embodiments of FIGS. 6A to 6U, the distal cutting edge of the distal cutting end 203b comprises twelve teeth, with two pairs of six right triangular teeth disposed on opposite sides of the central longitudinal axis 209. The distal teeth of twelve teeth are arranged to form a straight line perpendicular to the central longitudinal axis 209.

FIG. 6A shows the distal cutting edge 203b brought into contact with the bone B such that the distal cutting edge is tangent to the center part of the exterior of the bone B. The exterior of bone B, which may be, for example, a femur or a tibia, is typically rounded. Thus, only the left central tooth 220A1 and the right central tooth 220B1. As the cycle of oscillation of the distal cutting edge 203b starts, the distal cutting edge 203b moves toward the right as indicated by right-facing arrow 60.

FIG. 6B shows the distal cutting edge 203b as it progresses through the cycle of oscillation from the time point shown in the previous figure, FIG. 6A. As the distal cutting edge 203b moves to the right, the left central tooth 220A1 has begun to cut bone B, the left next to center tooth 220A2 contacts the exterior of the bone B, and the right central tooth 220B1 has begun to move away from the exterior of the bone B, giving more space for the bone chips cut by the left central tooth 220A1 to be brushed away.

FIG. 6C shows the distal cutting edge 203b as it progresses through the cycle of oscillation from the time point shown in the previous figure, FIG. 6B. As the distal cutting edge 203b continues to move to the right, the left central tooth 220A1 continues to cut bone B, the left next to center tooth 220A2 has begun to cut bone B, and the left next to next to center tooth 220A3 contacts the exterior of bone B.

FIG. 6D shows the distal cutting edge 203b as it progresses through the cycle of oscillation from the time point shown in the previous figure, FIG. 6C. As the distal cutting edge 203b continues to move to the right, the left center tooth 220A1 and the left next to center tooth 220A2 continue to cut bone B, the left next to next to center tooth 220A3 starts to cut bone B, and the left middle tooth 220A4 contacts the exterior of bone B.

FIG. 6E shows the distal cutting edge 203b as it progresses through the cycle of oscillation from the time point shown in the previous figure, FIG. 6D. As the distal cutting edge 203b continues to move to the right, the left center tooth 220A1, the left next to center tooth 220A2, and the left next to next to center tooth 220A4 continue to cut bone B and the left middle outer tooth 220A5 contacts the exterior of bone B.

FIG. 6F shows the distal cutting edge 203b as it progresses through the cycle of oscillation from the time point shown in the previous figure, FIG. 6E. As the distal cutting edge 203b continues to move to the right, the left center tooth 220A1, the left next to center tooth 220A2, the left next to next to center tooth 220A4, and the left middle outer tooth 220A5 continue to cut bone B and the left outer tooth 220A6 contacts the exterior of bone B.

FIG. 6G shows the distal cutting edge 203b as it progresses through the cycle of oscillation from the time point shown in the previous figure, FIG. 6F. As the distal cutting edge 203b continues to move to the right, the left center tooth 220A1, the left next to center tooth 220A2, the left next to next to center tooth 220A4, the left middle outer tooth 220A5, and the left outer tooth 220A6 continue to cut bone B.

FIG. 6H shows the distal cutting edge 203b as it progresses through the cycle of oscillation from the time point shown in the previous figure, FIG. 6G. The distal cutting edge 203b having reached its right most position, reverses its course and begins to move to the left as indicated by left-facing arrow 61. The distal cutting edge 203b may be advanced slightly toward the bone B as its direction reverses. The left center tooth 220A1, the left next to center tooth 220A2, the left next to next to center tooth 220A3, the left middle tooth 220A4, and the left middle outer tooth 220A5 continue to cut bone B but from the opposite direction. The left outer tooth 220A6 begins to move away from contacting the exterior of bone B, providing an evacuation window for bone chips, and begins to cool as it experiences less friction. The right center tooth 220B1 begins to contact the exterior of the bone B.

FIG. 6I shows the cutting edge 203b as it progresses through the cycle of oscillation from the time point shown in the previous figure, FIG. 6H. As the distal cutting edge 203b continues to move to the left, the left center tooth 220A1, the left next to center tooth 220A2, the left next to next to center tooth 220A3, the left middle tooth 220A4, and the left middle outer tooth 220A5 finish up cutting their respective portions of bone B. The right center tooth 220B1 begins to cut bone B and the right next to center tooth 220B2 begins to contact the exterior of bone B.

FIG. 6J shows the cutting edge 203b as it progresses through the cycle of oscillation from the time point shown in the previous figure, FIG. 6H. Each of the left teeth 220A1, 220A2, 220A3, 220A4, 220A5 and 220A6 have finished cutting their respective portions of bone B and have begun to or are already moved away from contacting the exterior of the bone B. As these teeth now experience less friction, they begin to cool. The right center tooth 220B1 and the right next to center tooth 220B2 continue to cut their respective portions of bone B.

FIGS. 6K to 6S show the cutting edge 203b as it sequentially progresses through the cycle of oscillation from the time point shown in their respective previous figures. As the distal cutting edge 203b continues to move to the left, the right center tooth 220B1, right next to center tooth 220B2, the right next to next to center tooth 220B3, the right middle tooth 220B4, the right middle outer tooth 220B5, and the right outer tooth 220B6 sequentially and progressively contact and cut the bone B similarly to the left teeth 220A1, 220A2, 220A3, 220A4, 220A5 and 220A6 previously described. The left teeth 220A1, 220A2, 220A3, 220A4, 220A5 and 220A6 progressively move away from the bone B, allowing these teeth to experience less friction and continue to cool. This also give additional space for the bone chips cut by right teeth 220B1, 220B2, 220B3, 220B4, 220B5 and 220B6 to be brushed away.

FIG. 6S shows the cutting edge 203b as it reaches its left most position, completing one full cycle of oscillation. Thereafter, the cutting edge 203b reverses its course and moves toward the right. The cutting edge 203b may be slightly advanced toward the bone B as its direction changes. The right teeth 220B1, 220B2, 220B3, 220B4, 220B5 and 220B6 progressively cut in the opposite direction from before and then move away from the bone B. The left teeth 220A1, 220A2, 220A3, 220A4, 220A5 and 220A6 progressively contact and cut the bone B as described above. As each tooth cuts the bone B, its respective opposite tooth (for example, left outer tooth 220A6 is opposite right outer tooth 220B6) is finished cutting and is cooled and cleaned of chips. Cycles of oscillation continues until the cut desired by the surgeon is completed.

FIG. 6T shows the cut or kerf on bone B. FIG. 6U shows a magnified view of the cut or kerf on bone B. The cutting edge 203b has been retracted to better show the cut or curf in FIGS. 6T and 6U. The kerf has a staircase shape and is slightly V-shaped or convex. The kerf generally approximates the straight line of the distal tips of the teeth of the distal cutting edge 205. In addition to the long pivot radius of the elongate monolithic blade 203, the progressive cutting from the teeth of cutting edge 203b by the "flat-top" arrangement of these teeth result in the impact angle of the teeth and thus the angle 302 of the kerf being quite shallow. As angle 302 of the kerf is much shallower than that of those made by known surgical saws, it lends accuracy and stability to the surgical bone cutting performed by the surgeon.

Figure 7:
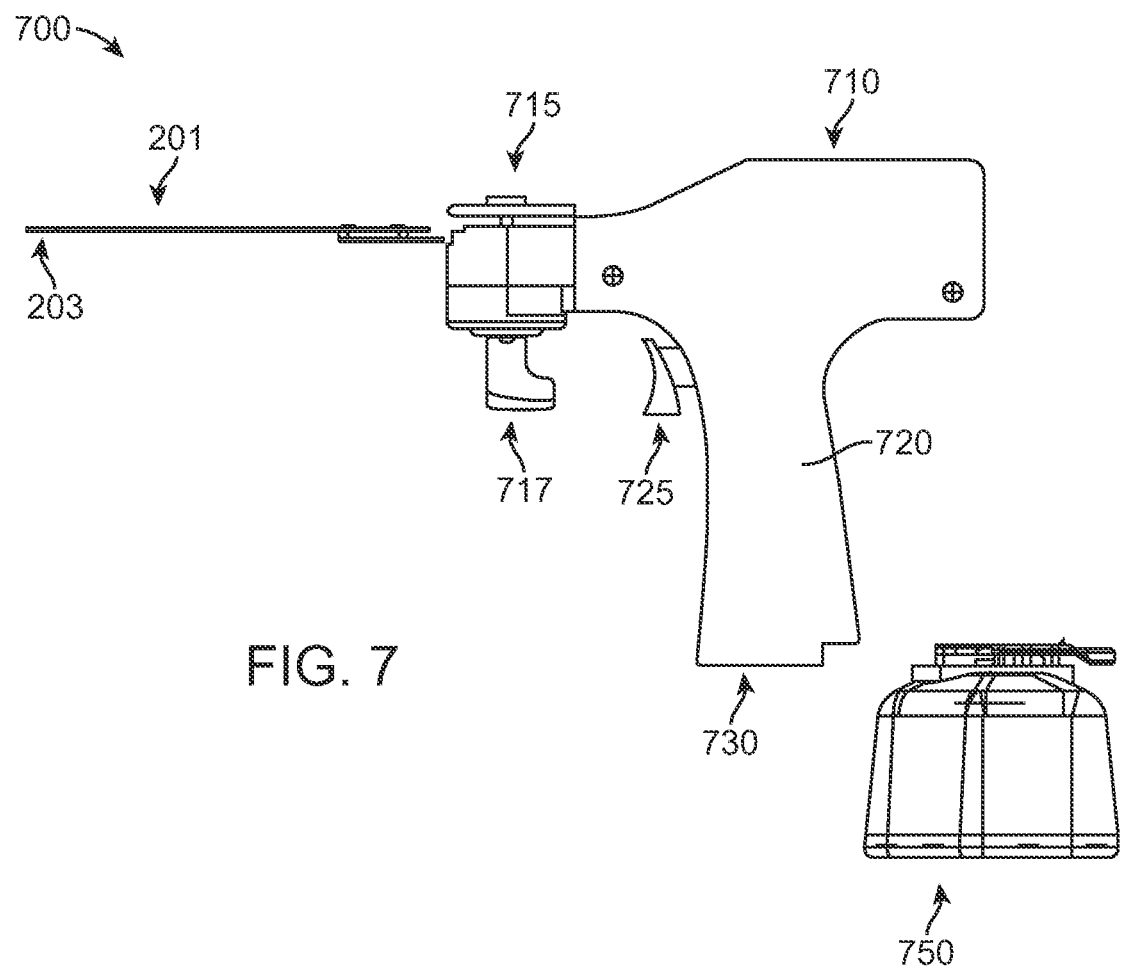
FIG. 7 shows a perspective view of a surgical saw blade system according to embodiments of the invention, including the surgical saw blade assembly of FIG. 2A and a hand holdable drive unit.
Figure 7A:
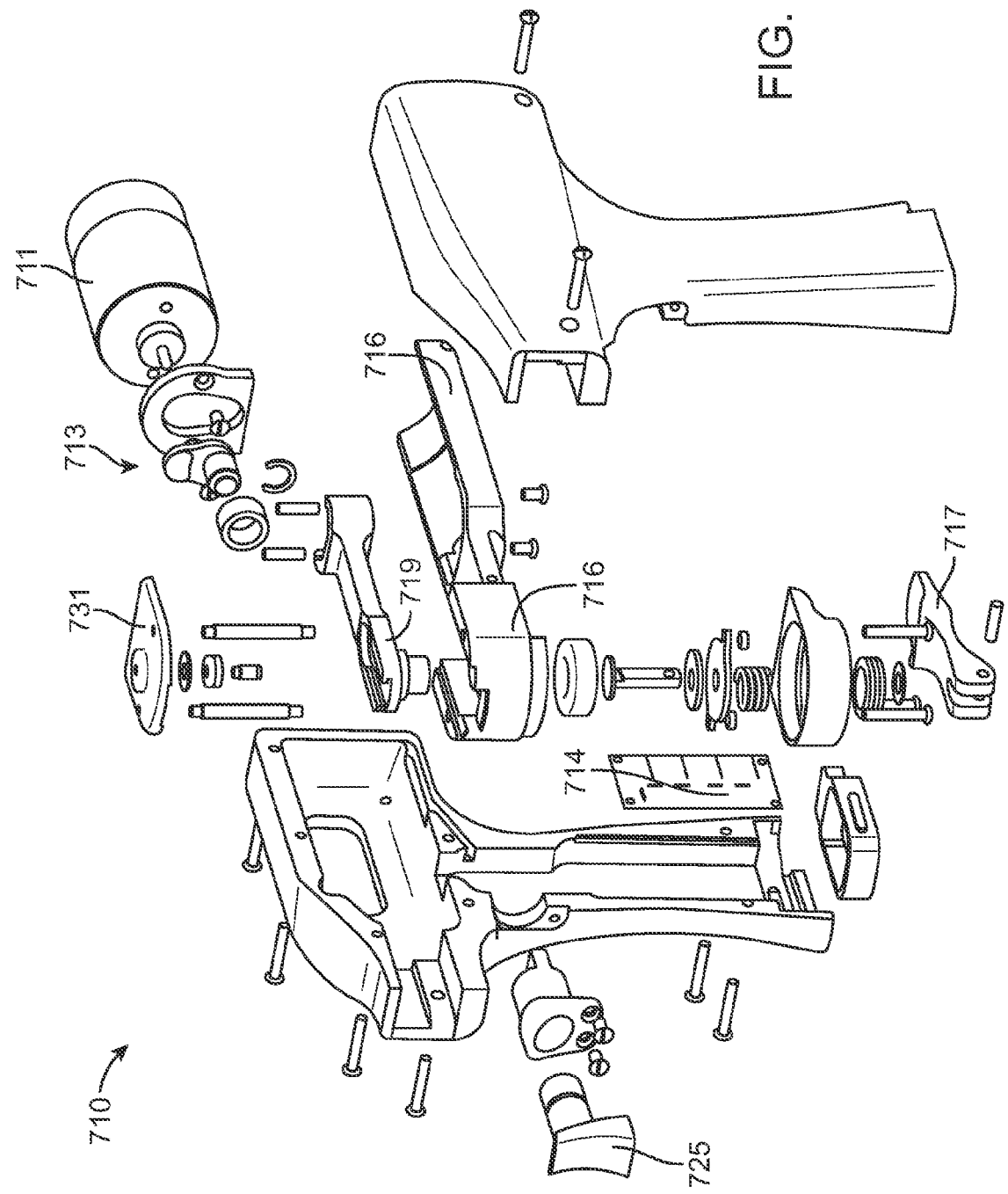
FIG. 7A shows an exploded view of the hand holdable drive unit of FIG. 7.
Figure 7B:
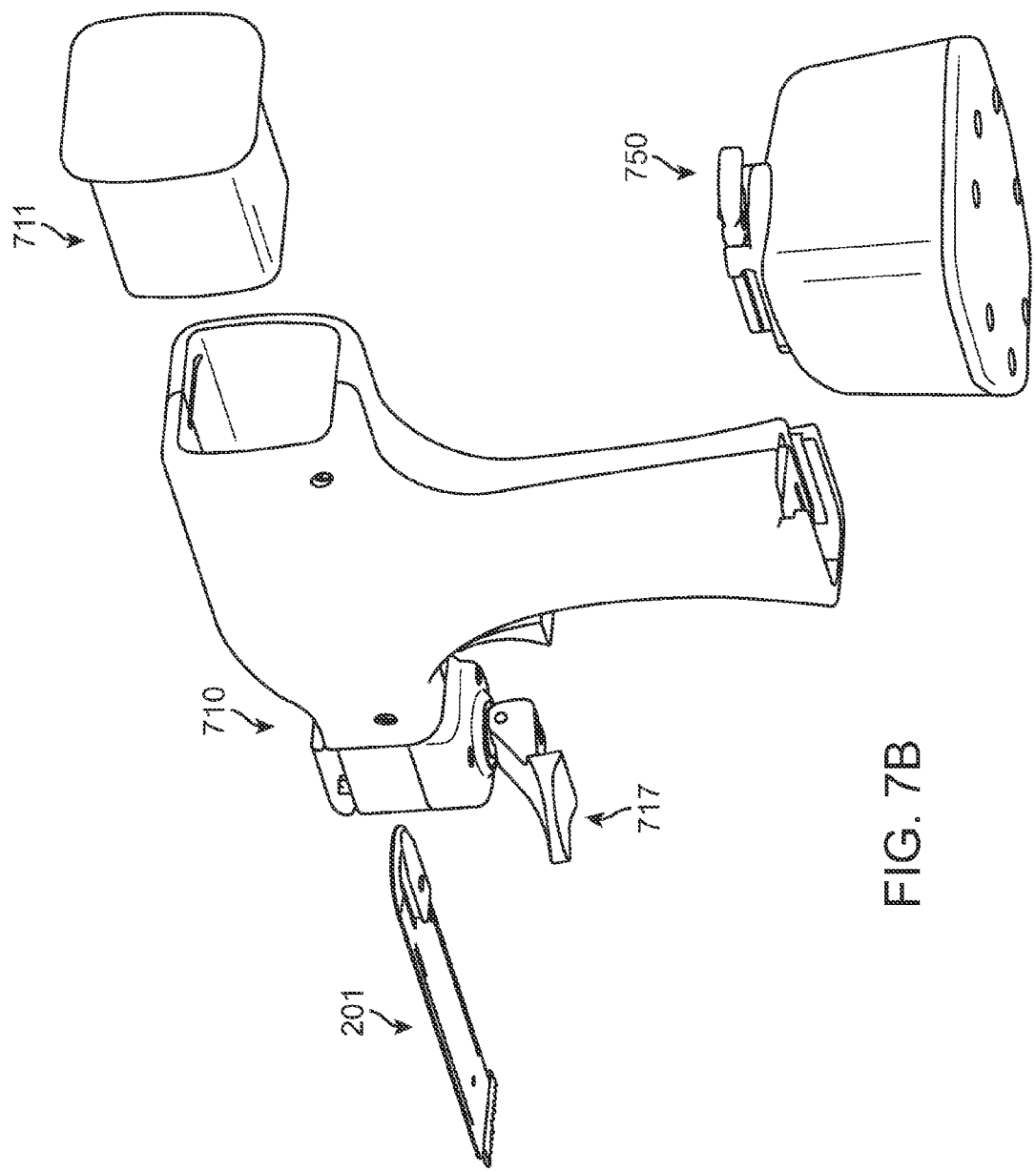
FIG. 7B shows a perspective view of a surgical saw blade system according to embodiments of the invention, including the surgical saw blade assembly of FIG. 2A and a hand holdable drive unit with a removable electric motor.

FIG. 7 shows a surgical saw blade system 700 according to embodiments of the invention. The surgical saw blade system 700 includes the surgical saw blade assembly 201, a hand holdable drive unit 710, and a battery pack 750. FIG. 7A shows an exploded view of the hand holdable drive unit 710. The hand holdable drive unit 710 comprises an internal electric motor 711, an internal eccentric mechanism 713, circuitry 714, a locking mechanism 715 (having a main body 716, a lever 717, and an internal oscillating member 719), a hand holdable portion 720, a trigger 725, and a battery interface at its bottom 730. The battery pack 750 can be removeably coupled to the hand holdable drive unit 710 to power it. Typically, the hand holdable drive unit 710 and the battery pack 750 are configured so that the battery pack 750 slides into the bottom 730 of the hand holdable drive unit 710. In some embodiments, for example as shown in FIG. 7B, the internal electric motor 711 may be removable from the hand holdable drive unit 710 so that it can be easily removed, disposed, and replaced, for example, after a single use. Alternatively or in combination, the hand holdable drive unit 710 may be disposed after a single use while the removable electric motor 711 is provided as a reusable motor pack.

The surgical saw blade assembly 201 is removably coupleable with the hand holdable drive unit 710 through the locking mechanism 715, which has an unlocked configuration in which the surgical saw blade assembly 201 can be inserted therein and a locked configuration which tightly holds the surgical saw blade assembly 201. The lever 717 can be used to toggle the linkage mechanism 715 between the unlocked and locked configurations. In the locked configuration, the proximal end 203b of the elongate monolithic blade 203 is tightly mounted on the oscillating member 719. When the surgical saw blade assembly 201 is coupled with the hand holdable drive unit 710, pulling the trigger 725 causes the elongate monolithic blade 203 of the surgical saw blade assembly 201 to oscillate and cut a target object. Pulling the trigger 725 causes the circuitry 714 to draw power from the attached battery pack 750 and activate the internal electric motor 711. The internal electric motor in turn actuates the internal eccentric mechanism 713, which causes the oscillating member 719 and thus the coupled elongate monolithic blade 203 to oscillate. At the same time, the main body 716 of the locking mechanism 715 holds the elongate sheath 204 stationary. Thus, target tissues are only exposed to the cutting motions of the distal cutting end 203b of the elongate monolithic blade 203.

In many embodiments, the hand holdable drive unit 710 will be mostly made of injection molded plastic, making the drive unit light-weight, low cost, and disposable. Further, the internal eccentric mechanism 713 can be made of lightweight aluminum and can comprise ceramic bearing surfaces. In addition to making the hand-held drive unit light-weight and low cost, the materials of the hand-held drive unit may be selected reduce the amount of noise the drive unit makes while activated. For example, the hand holdable drive unit 710 may be at least partially made of a sound absorbent resin. Alternatively or in combination, the hand holdable drive unit 710 and/or the locking mechanism 715 can be covered in a noise absorbent sheath.

Figure 8A:
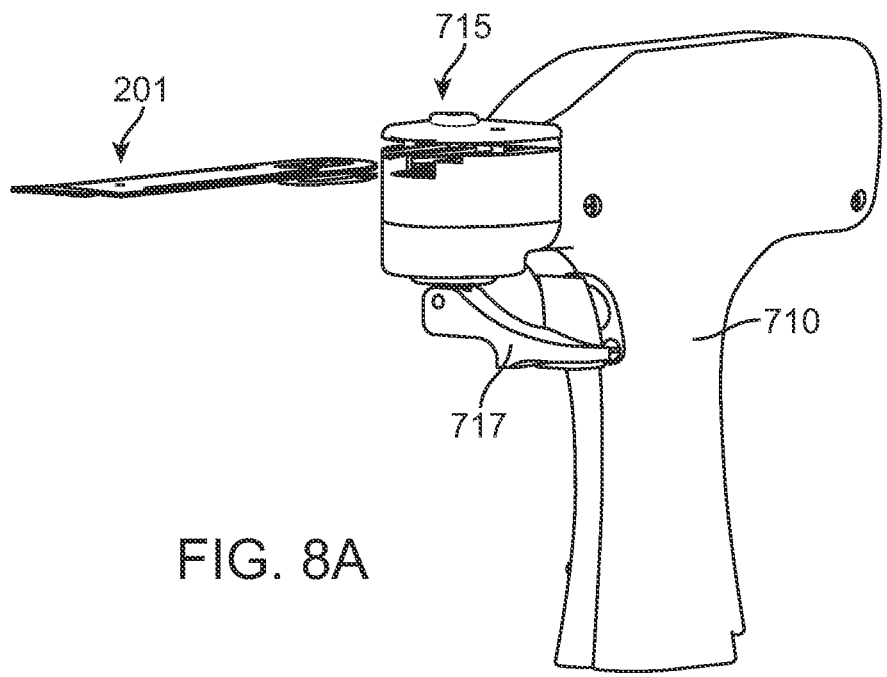
FIG. 8A shows a perspective view of the surgical saw blade assembly of FIG. 2A and the hand holdable drive unit of FIG. 7 in its unlocked configuration.
Figure 8B:
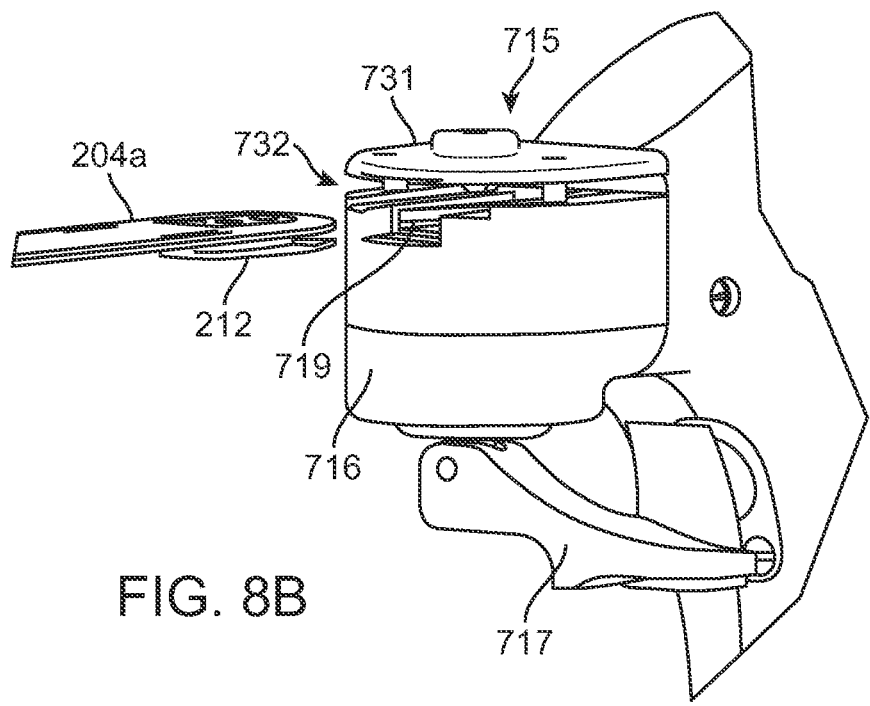
FIG. 8B is a magnified view of the locking mechanism of the hand holdable drive unit of FIG. 8A.

FIG. 8A shows the locking mechanism 715 in its unlocked configuration. FIG. 8B shows this with a magnified view. The locking mechanism further comprises a top portion 731. The top portion 731 helps form a saw blade assembly reception slot 732, comprising a portion of the oscillating member 719 shaped to be an exact match to the drive unit coupling member 212 of the surgical saw blade assembly 201 and a portion of the main body 716 shaped to be an exact match for the U-shaped proximal end 204b of the surgical saw blade assembly 201.

Figure 9A:
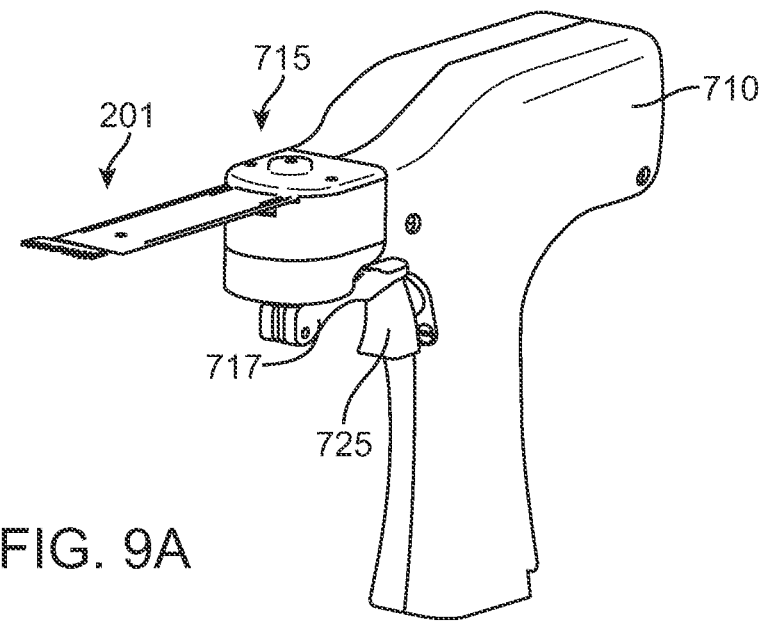
FIG. 9A shows a perspective view of the surgical saw blade assembly of FIG. 2A and the hand holdable drive unit of FIG. 7 in its locked configuration.
Figure 9B:
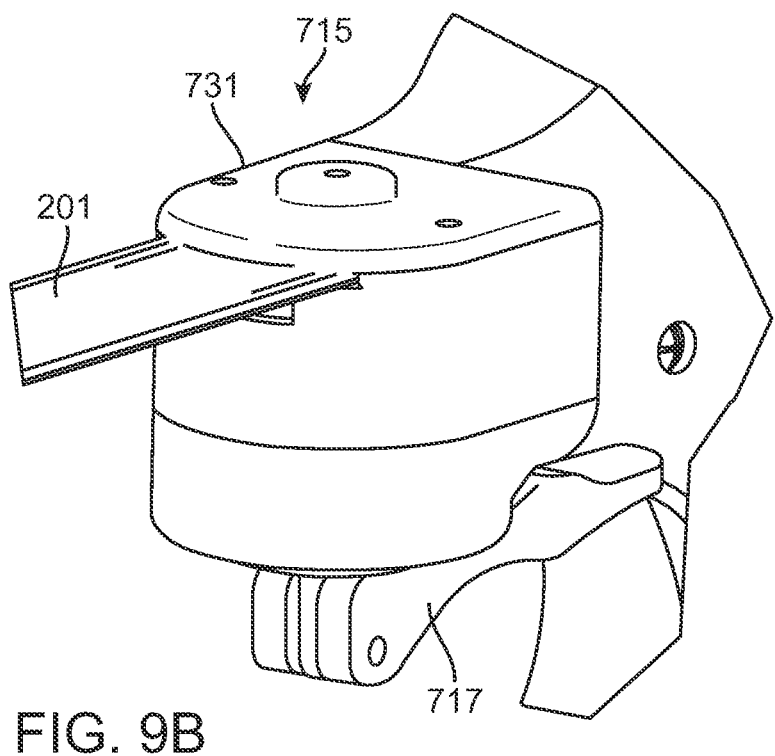
FIG. 9B is a magnified view of the locking mechanism of the hand holdable drive unit of FIG. 8A.

FIG. 9A shows the locking mechanism 715 in its locked configuration locking in the surgical saw blade assembly 201. FIG. 9B shows this with a magnified view. Moving the lever 717 from its position as shown in FIGS. 8A and 8B to its position shown in FIGS. 9A and 9B has moved and locked the top portion 731 in close contact with the main body 716.

Figure 10:
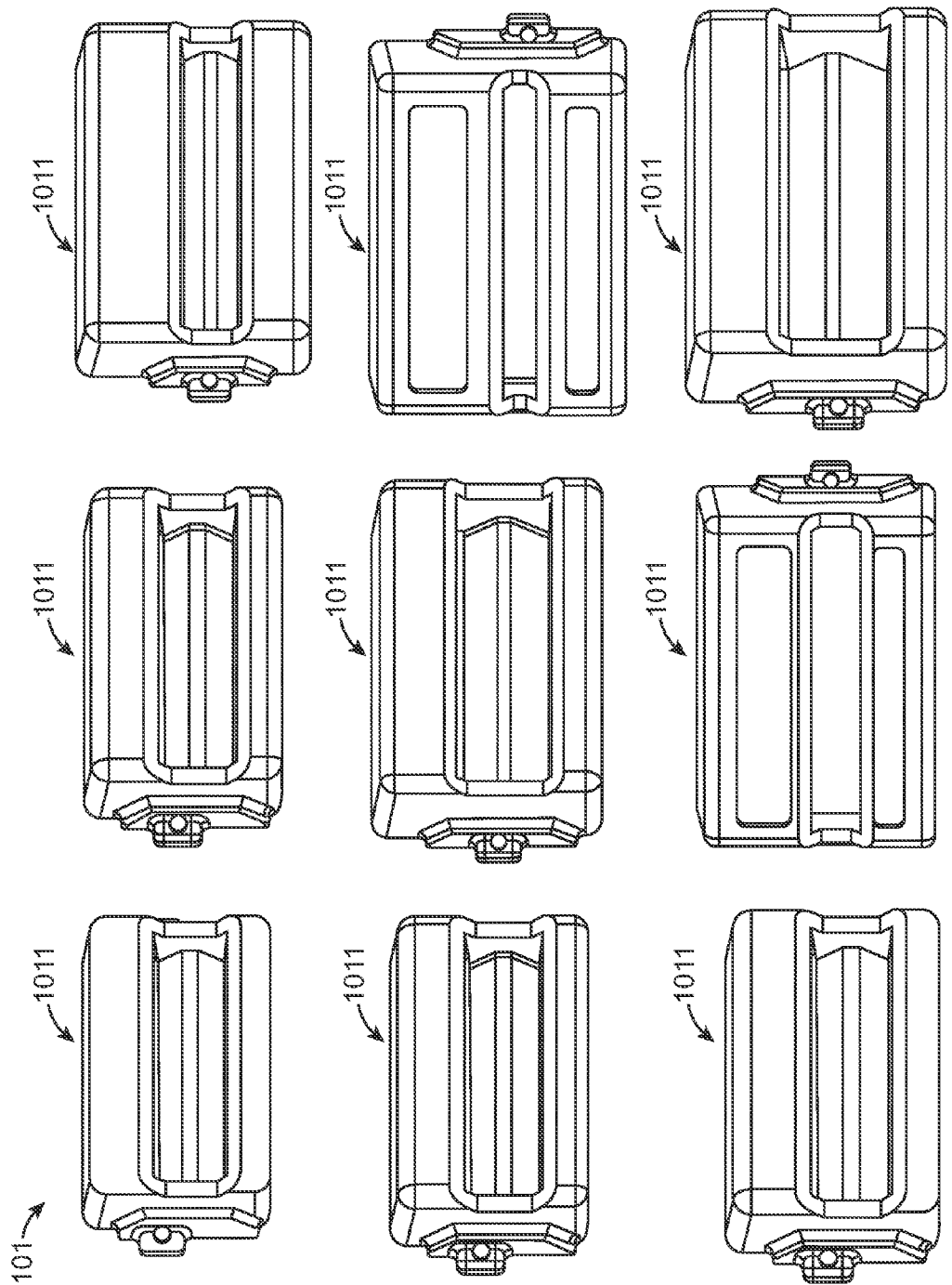
FIG. 10 shows a surgical saw blade kit according to embodiments of the invention.

In many embodiments, the surgical saw blade system 700 may be provided, e.g., sold, in a kit. FIG. 10 shows an exemplary surgical saw blade kit 101. The surgical saw blade kit comprises the hand holdable drive unit 710, the battery pack 750, and a plurality of surgical saw blade assemblies 201 each configured to couple with the drive unit 710. The surgical saw blade kit may further comprise a plurality of sheathless monolithic surgical saw blades 270 configured to couple with the drive unit 710. Each of the surgical saw blade assemblies 201 and sheathless monolithic surgical saw blades 270 may have distal cutting ends 203b of different sizes, shapes, materials, cutting edge arrangement, teeth size, teeth shape, teeth number, etc. for different bone cutting applications. For example, a sheathless monolithic surgical saw blade 270a may comprise a plurality of elongate support member 276. In some embodiments, the surgical saw blade kit 101 may further comprise at least one cutting guide 1011. The cutting guides 1011 will typically fit on the cut end of a patient's femur or tibia to facilitate the correct positioning of bone cuts. The cutting guides 1011 may be similar to those shown in U.S. Design patent No. 29/335,690.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A saw blade assembly for use with a driver having an oscillatory drive member for performing surgical cuts to bone tissue with minimal injury to surrounding tissue, said saw blade assembly comprising:

an elongate sheath having a proximal end, a distal end, a first side, an opposing second side, an open interior defined between the first side and the second side, and an aperture through one of the first side and the second side, said proximal end being removably mountable on the driver to be held stationary relative to the driver when said saw blade assembly performs surgical cuts;

an elongate monolithic blade received within the open interior of the sheath, said monolithic blade having a unitary construction, with no moveably connected parts, a central longitudinal axis, a proximal end that extends through the aperture of the elongate sheath to removably couple to the oscillatory drive member of the driver when the proximal end of the elongate sheath is mounted on the driver, a single pivot point located at the proximal end, a first side, an opposing second side, and a distal cutting end transverse to the central longitudinal axis and extending from the distal end of the sheath;

wherein the first side of the blade faces the first side of the sheath and the second side of the blade faces the second side of the sheath;

wherein a majority of the blade is housed within the interior of the sheath, wherein the sheath has no moving internal parts other than the elongate monolithic blade; and wherein the oscillatory drive member pivots the distal cutting end back and forth about the pivot point at the proximal end of the monolithic blade when the proximal end of the monolithic blade is coupled to the oscillatory drive member to perform surgical cuts.

2. The saw blade assembly of claim 1, wherein the distal cutting end is configured to engage bone tissue at an angle of less than about 10 degrees.

3. The saw blade assembly of claim 2, wherein the distal cutting end is configured to engage bone tissue at an angle of less than about 6 degrees.

4. The saw blade assembly of claim 3, wherein the distal cutting end is configured to engage bone tissue at an angle of less than about 3 degrees.

5. The saw blade assembly of claim 1, wherein the saw blade assembly further comprises at least one elongate support rib.

6. The saw blade assembly of claim 5, wherein the at least one elongate support rib is coupled to the elongate sheath.

7. The saw blade assembly of claim 5, wherein the at least one elongate support rib is formed in the elongate sheath.

8. The saw blade assembly of claim 1, wherein the distal cutting end of the monolithic blade is perpendicular to the central longitudinal axis of the monolithic blade.

9. The saw blade assembly of claim 1, wherein the distal cutting end of the monolithic blade comprises a plurality of teeth, each tooth comprising a distal tip.

10. The saw blade assembly of claim 9, wherein the tips of each tooth are positioned on a single straight line perpendicular to the central longitudinal axis of the elongate monolithic blade.

11. The saw blade assembly of claim 9, wherein each tooth is identically shaped.

12. The saw blade assembly of claim 9, wherein the plurality of teeth comprises an even number of teeth.

13. The saw blade assembly of claim 9, wherein each tooth is shaped as a right triangle, each tooth having a right angle, a hypotenuse opposite the right angle, and a longitudinal side adjacent the hypotenuse, wherein the right angle of each tooth is oriented at least one of toward or away from the central longitudinal axis of the blade.

14. The saw blade assembly of claim 13, wherein the longitudinal side of each tooth is disposed along a radial line extending from the tip of the tooth to the pivot point at the proximal end of the monolithic blade.

15. The saw blade assembly of claim 13, wherein the longitudinal sides of each tooth are parallel with one another.

16. The saw blade assembly of claim 13, wherein the right angle of each tooth is oriented away from the central longitudinal axis of the monolithic blade.

17. The saw blade assembly of claim 16, wherein the distal cutting end further comprises a centrally positioned tooth shaped as an isosceles triangle, said centrally positioned tooth being formed by two right triangular teeth sharing the same longitudinal side disposed along the central longitudinal axis of the blade.

18. The saw blade assembly of claim 13, wherein the cutting surface further comprises a centrally positioned tooth shaped as an isosceles triangle.

19. The saw blade assembly of claim 9, wherein the tips of the plurality of teeth are disposed along an arc centered about the pivot point at the proximal end of the monolithic blade.

20. The saw blade assembly of claim 9, wherein each tooth is identically shaped as an approximately isosceles triangle and the tips of the plurality of teeth are disposed along a lateral line perpendicular to the central longitudinal axis of the monolithic blade.

21. The saw blade assembly of claim 9, wherein the plurality of teeth comprises a plurality of inner teeth and a plurality of outer teeth, and wherein the tips of the plurality of inner teeth are disposed on a first single straight line perpendicular to the central longitudinal axis, the tips of the plurality of the outer teeth are disposed on a second single straight line perpendicular to the central longitudinal axis, the first single straight line being different than the second single straight line.

22. The saw blade assembly of claim 1, wherein at least a portion of the monolithic blade comprises at least one of metal, stainless steel, composite, carbon fiber composite, polymer, titanium, or ceramic.

23. A surgical saw system for performing surgical cuts to bone tissue with minimal injury to surrounding tissue, the surgical saw system comprising:
the saw blade assembly of claim 1; and
a drive assembly comprising the driver having the oscillatory drive member, said drive assembly being configured to couple to the saw blade assembly to pivotably drive the monolithic blade of the saw blade assembly to cut tissue.

24. The surgical saw system of claim 23, further comprising an external battery pack coupleable to the drive assembly to power the drive assembly.

25. The surgical saw system of claim 23, wherein the drive assembly is hand-holdable.

26. The surgical saw system of claim 23, wherein the drive assembly comprises a locking mechanism having an open configuration and a closed configuration, wherein the saw blade assembly is insertable into the locking mechanism in the open configuration to couple the saw blade assembly to the drive assembly, and wherein the locking mechanism in the closed configuration holds the sheath of the saw blade assembly stationary relative to the driver and couples to the elongate monolithic blade when the drive assembly is coupled to the saw blade assembly.

27. The surgical saw system of claim 26, wherein the locking mechanism comprises a lever actuatable to switch the locking mechanism between the open and closed configurations.

28. The surgical saw system of claim 26, wherein the proximal end of the monolithic blade defines an aperture at the pivot point, and wherein the linkage mechanism comprises a knob which fits into the aperture of the proximal end of the monolithic blade when the linkage mechanism is in the closed configuration when the drive assembly is coupled to the saw blade assembly.

29. The surgical saw system of claim 26, wherein the locking mechanism comprises a saw blade assembly slot adapted to hold a proximal end of the saw blade assembly stationary relative to the driver when the saw blade assembly is inserted into the locking mechanism.

30. The surgical saw system of claim 23, wherein the oscillatory drive member comprises a blade slot adapted to hold the proximal end of the monolithic blade when the saw blade assembly is inserted into the locking mechanism.

31. The surgical saw system of claim 23, wherein the drive assembly comprises an electric motor and an eccentric mechanism coupled to the electric motor.

32. The surgical saw system of claim 31, wherein the eccentric mechanism is coupled to the oscillatory drive member to oscillate the blade about the pivot point when the saw blade assembly is coupled to the drive assembly.

33. The surgical saw system of claim 31, wherein the drive assembly further comprises a trigger pressable to activate the electric motor.

34. The surgical saw system of claim 31, wherein the electric motor is removable from the drive assembly.

35. The surgical saw system of claim 23, further comprising a noise absorbent sheath for covering at least a portion of the drive assembly.

36. The surgical saw system of claim 23, further comprising at least one cutting guide configured to guide the saw blade assembly in cutting bone tissue.

37. A saw blade assembly for use with a driver having an oscillatory drive member and for performing surgical cuts to bone tissue with minimal injury to surrounding tissue, the saw blade assembly comprising:
an elongate sheath having a proximal end, a distal end, and an aperture through one side, the proximal end being mountable on the driver to be held stationary relative to the driver when said saw blade assembly performs surgical cuts; and
an elongate monolithic blade, a majority of which is disposed within the sheath, wherein the blade has a unitary construction, with no moveably connected parts, a central longitudinal axis, a proximal end that extends through the aperture of the elongate sheath to removably couple the blade to the oscillatory drive member of the driver when the proximal end of the elongate sheath is mounted on the driver, and a distal cutting end transverse to the central longitudinal axis and extending from the distal end of the sheath,
wherein the one side extends substantially parallel to a top surface of the blade,
wherein the oscillatory drive member pivots the distal cutting end back and forth about a pivot point at the proximal end of the monolithic blade when the proximal end of the monolithic blade is coupled to the oscillatory drive member to perform surgical cuts, and wherein the sheath has no moving internal parts other than the elongate monolithic blade.

* * * * *